United States Patent
Kremsky et al.

(10) Patent No.: US 11,787,830 B2
(45) Date of Patent: Oct. 17, 2023

(54) CRYSTALLINE SOLIDS OF NICOTINIC ACID MONONUCLEOTIDE AND ESTERS THEREOF AND METHODS OF MAKING AND USE

(71) Applicant: Metro International Biotech, LLC, Cambridge, MA (US)

(72) Inventors: Jonathan N. Kremsky, Worcester, MA (US); Bruce Szczepankiewicz, Worcester, MA (US); Karsten Koppetsch, Worcester, MA (US); Joseph Harris, Cambridge (GB); Mateusz Pitak, Cambridge (GB); Martin Bates, Cambridge (GB)

(73) Assignee: Metro International Biotech, LLC, Worcester, MA (US)

( * ) Notice: Subject to any disclaimer, the term of this patent is extended or adjusted under 35 U.S.C. 154(b) by 0 days.

(21) Appl. No.: 18/129,345

(22) Filed: Mar. 31, 2023

(65) Prior Publication Data
US 2023/0257412 A1    Aug. 17, 2023

Related U.S. Application Data

(63) Continuation of application No. PCT/US2022/031124, filed on May 26, 2022.

(60) Provisional application No. 63/193,905, filed on May 27, 2021.

(51) Int. Cl.
| C07H 19/048 | (2006.01) |
| A61K 31/706 | (2006.01) |
| C30B 7/02 | (2006.01) |
| C07H 1/06 | (2006.01) |

(52) U.S. Cl.
CPC ......... *C07H 19/048* (2013.01); *A61K 31/706* (2013.01); *C07H 1/06* (2013.01); *C30B 7/02* (2013.01)

(58) Field of Classification Search
None
See application file for complete search history.

(56) References Cited

U.S. PATENT DOCUMENTS

| 3,201,389 A | 8/1965 | Fujjimoto et al. |
| 3,451,997 A | 6/1969 | Fujimoto et al. |
| 4,411,995 A | 10/1983 | Whitesides et al. |
| 7,560,442 B2 | 7/2009 | Susilo |
| 7,776,326 B2 | 8/2010 | Milbrandt et al. |
| 7,977,049 B2 | 7/2011 | Sinclair et al. |
| 8,481,711 B2 | 7/2013 | Kaminishi et al. |
| 9,169,209 B2 | 10/2015 | Bair et al. |
| 9,295,688 B2 | 3/2016 | Milbrandt et al. |
| 9,458,172 B2 | 10/2016 | Bair et al. |
| 9,676,721 B2 | 6/2017 | Bair et al. |
| 9,822,129 B2 | 11/2017 | Bair et al. |
| 9,855,289 B2 | 1/2018 | Normington et al. |
| 9,861,651 B2 | 1/2018 | Brown et al. |

(Continued)

FOREIGN PATENT DOCUMENTS

| CN | 101497638 A | 8/2009 |
| CN | 101601679 B | 8/2011 |

(Continued)

OTHER PUBLICATIONS

Ahmadibeni et al., "Solid-Phase Synthesis of Symmetrical 5',5'-Dinucleoside Mono-, Di-, Tri-, and Tetraphosphodiesters," Organic Letters, 9(22): 4483-4486 (2007).

(Continued)

*Primary Examiner* — Layla D Berry
(74) *Attorney, Agent, or Firm* — Foley Hoag LLP; David P. Halstead

(57) ABSTRACT

The present disclosure relates to crystalline solids comprising a compound of Formula (I),

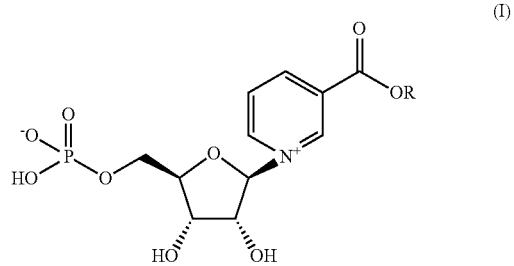

wherein R is n-propyl, and methods of making compounds of Formula (I) wherein R is C1-C4 alkyl or C2-C4 alkenyl. The present disclosure also relates to crystalline solids comprising a compound of Formula (II),

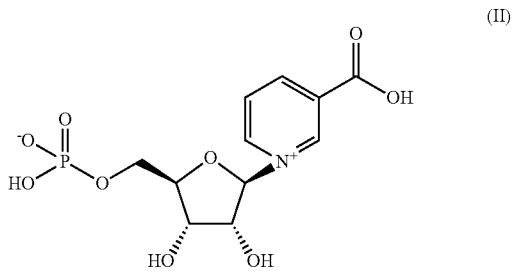

The present disclosure further relates to methods of preparing the crystalline solids, and pharmaceutical preparations of the crystalline solids, and use of such pharmaceutical preparations in treatment of diseases and conditions.

21 Claims, 7 Drawing Sheets

(56) References Cited

U.S. PATENT DOCUMENTS

| | | | |
|---|---|---|---|
| 9,919,003 | B2 | 3/2018 | Normington et al. |
| 9,975,915 | B1 | 5/2018 | Migaud et al. |
| 10,000,519 | B2 | 6/2018 | Migaud et al. |
| 10,214,552 | B2 | 2/2019 | Fu et al. |
| 10,233,208 | B1 | 3/2019 | Carr et al. |
| 10,392,415 | B2 | 8/2019 | Livingston et al. |
| 10,392,416 | B2 | 8/2019 | Livingston et al. |
| 10,548,913 | B2 | 2/2020 | Normington et al. |
| 10,618,927 | B1 | 4/2020 | Szczepankiewicz et al. |
| 11,059,847 | B2 | 7/2021 | Livingston et al. |
| 11,180,521 | B2 | 11/2021 | Kremsky et al. |
| 11,464,796 | B2 | 10/2022 | Normington et al. |
| 2004/0224039 | A1 | 11/2004 | Brucker |
| 2008/0318892 | A1 | 12/2008 | Pickering et al. |
| 2012/0107888 | A1 | 5/2012 | Schmalisch et al. |
| 2012/0328526 | A1 | 12/2012 | Kristian |
| 2013/0102771 | A1 | 4/2013 | Kaminishi et al. |
| 2013/0273034 | A1 | 10/2013 | Bair et al. |
| 2013/0295051 | A1 | 11/2013 | Bair et al. |
| 2014/0275057 | A1 | 9/2014 | Bair et al. |
| 2014/0294805 | A1 | 10/2014 | Bair et al. |
| 2015/0104384 | A1 | 4/2015 | Bair et al. |
| 2015/0132280 | A1 | 5/2015 | Lopez et al. |
| 2015/0175621 | A1 | 6/2015 | Bair et al. |
| 2015/0258052 | A1 | 9/2015 | Evans et al. |
| 2016/0002266 | A1 | 1/2016 | Bair et al. |
| 2016/0022712 | A1 | 1/2016 | Imai et al. |
| 2016/0168184 | A1 | 6/2016 | Migaud et al. |
| 2016/0287621 | A1 | 10/2016 | Sinclair et al. |
| 2016/0333041 | A1 | 11/2016 | Fu et al. |
| 2016/0355514 | A1 | 12/2016 | Bair et al. |
| 2016/0355539 | A1 | 12/2016 | Migaud et al. |
| 2017/0066724 | A1 | 3/2017 | Evans et al. |
| 2017/0182076 | A1 | 6/2017 | Alvarez et al. |
| 2017/0189433 | A1* | 7/2017 | Szczepankiewicz ...... A61P 3/10 |
| 2017/0204131 | A1 | 7/2017 | Szczepankiewicz et al. |
| 2017/0210774 | A1 | 7/2017 | Carlson et al. |
| 2017/0216262 | A1 | 8/2017 | Bair et al. |
| 2017/0267709 | A1 | 9/2017 | Migaud et al. |
| 2017/0304338 | A1 | 10/2017 | Dellinger et al. |
| 2017/0368039 | A1 | 12/2017 | Kenneth et al. |
| 2018/0030079 | A1 | 2/2018 | Carlson et al. |
| 2018/0051253 | A1 | 2/2018 | Chen |
| 2018/0086783 | A1 | 3/2018 | Carlson et al. |
| 2018/0104248 | A1 | 4/2018 | Lopez et al. |
| 2018/0134743 | A1 | 5/2018 | Migaud et al. |
| 2018/0147227 | A1 | 5/2018 | Normington et al. |
| 2018/0162895 | A1 | 6/2018 | Fu et al. |
| 2018/0186824 | A1 | 7/2018 | Migaud et al. |
| 2018/0228824 | A1 | 8/2018 | Yoshino et al. |
| 2020/0031860 | A1 | 1/2020 | Sauve |
| 2020/0157136 | A1 | 5/2020 | Livingston et al. |
| 2020/0181188 | A1 | 6/2020 | Rhonemus et al. |
| 2020/0352966 | A1 | 11/2020 | Normington et al. |
| 2020/0368198 | A1 | 11/2020 | Wu et al. |
| 2021/0030908 | A1 | 2/2021 | Mason |
| 2022/0098229 | A1 | 3/2022 | Livingston et al. |
| 2022/0144880 | A1 | 5/2022 | Szczepankiewicz et al. |
| 2023/0158053 | A1 | 5/2023 | Normington et al. |

FOREIGN PATENT DOCUMENTS

| | | |
|---|---|---|
| CN | 102876759 A | 1/2013 |
| CN | 104367587 B | 6/2018 |
| JP | S41-12737 B2 | 7/1966 |
| JP | S41-15179 B2 | 8/1996 |
| WO | WO-2006/072809 A2 | 7/2006 |
| WO | WO-2010/135520 A1 | 11/2010 |
| WO | WO-2012004917 A1 | 1/2012 |
| WO | WO-2012031196 A1 | 3/2012 |
| WO | WO-2012031197 A1 | 3/2012 |
| WO | WO-2012031199 A1 | 3/2012 |
| WO | WO-2012/094343 A1 | 7/2012 |
| WO | WO-2012/150952 A1 | 11/2012 |
| WO | WO-2013/085555 A2 | 6/2013 |
| WO | WO-2013127266 A1 | 9/2013 |
| WO | WO-2013127267 A1 | 9/2013 |
| WO | WO-2013127268 A1 | 9/2013 |
| WO | WO-2013127269 A1 | 9/2013 |
| WO | WO-2013130943 A1 | 9/2013 |
| WO | WO-2014/059034 A2 | 4/2014 |
| WO | WO-2014/074715 A1 | 5/2014 |
| WO | WO-2014/111906 A1 | 7/2014 |
| WO | WO-2014/146044 A1 | 9/2014 |
| WO | WO-2015/014722 A1 | 2/2015 |
| WO | WO-2015/069860 A1 | 5/2015 |
| WO | WO-2015073576 A1 | 5/2015 |
| WO | WO-2015/138969 A1 | 9/2015 |
| WO | WO-2015/186068 A1 | 12/2015 |
| WO | WO-2016014927 A2 | 1/2016 |
| WO | WO-2016086860 A1 | 6/2016 |
| WO | WO-2016/144660 A1 | 9/2016 |
| WO | WO-2016196941 A1 | 12/2016 |
| WO | WO-2017022768 A1 | 2/2017 |
| WO | WO-2017/059249 A1 | 4/2017 |
| WO | WO-2017/062311 A1 | 4/2017 |
| WO | WO-2017/079195 A1 | 5/2017 |
| WO | WO-2017110317 A1 | 6/2017 |
| WO | WO-2017/114796 A1 | 7/2017 |
| WO | WO-2017145151 A1 | 8/2017 |
| WO | WO-2017/161165 A1 | 9/2017 |
| WO | WO-2017185549 A1 | 11/2017 |
| WO | WO-2017/218580 A1 | 12/2017 |
| WO | WO-2018023205 A1 | 2/2018 |
| WO | WO-2018023207 A1 | 2/2018 |
| WO | WO-2018023208 A1 | 2/2018 |
| WO | WO-2018023209 A1 | 2/2018 |
| WO | WO-2018023210 A1 | 2/2018 |
| WO | WO-2018/047715 A1 | 3/2018 |
| WO | WO-2018/047716 A1 | 3/2018 |
| WO | WO-2018/052019 A1 | 3/2018 |
| WO | WO-2018/052020 A1 | 5/2018 |
| WO | WO-2018/089830 A1 | 7/2018 |
| WO | WO-2018120069 A1 | 7/2018 |
| WO | WO-2018/132833 A1 | 8/2018 |
| WO | WO-2018/143258 A1 | 8/2018 |
| WO | WO-2019/152416 A1 | 8/2019 |
| WO | WO-2020/197882 A1 | 10/2020 |
| WO | WO-2022/251491 A1 | 12/2022 |

OTHER PUBLICATIONS

Anastasi et al., "New antiviral nucleoside prodrugs await application," Current medicinal chemistry, 10(18):1825-1843 (2003).

Asher et al., "SIRT1 Regulates Circadian Clock Gene Expression through PER2 Deacetylation," Cell, 134:317 (2008).

Atkinson et al., "Nicotinamide 6-Mercaptopurine Dinucleotide and Related Compounds: Potential Sources of 6-Mercaptopurine Nucleotide in Chemotherapy," Nature, 196: 35-36 (1962).

Barnea et al., "High-Fat Diet Delays and Fasting Advances the Circadian Expression of Adiponectin Signaling Components in Mouse Liver," Endicrinology 150:161 (2009).

Bauer, "Polymorphism—A Critical Consideration in Pharmaceutical Development, Manufacturing, and Stability," Journal of Validation of Technology, 14(5):15-23 (2008).

Bazzanini et al., "Synthetic approaches to a mononucleotide prodrug of cytarabine," Nucleosides, Nucleotides, and Nucleic Acids, 24(10-12):1635-1649 (2005).

Belenky et al., "Nicotinamide riboside promotes Sir2 silencing and extends lifespan via Nrk and Urh1/Pnp1/Meu1 pathways to NAD+," Cell, 129(3):473-484 (2007).

Berghaeuser et al., "A Simple Preparation of an Enzyme Reactor Producing Nicotinamidemononucleotide," Biotechnology Letters, 3(7): 339-344 (1981).

Bieganowski et al., "Discoveries of nicotinamide riboside as a nutrient and conserved NRK genes establish a preiss-handler independent route to NAD+ in fungi and humans," Cell, 117:495-502 (2004).

Bobeck et al., "Advances in nucleoside monophosphate prodrugs as anti-HCV agents," Antiviral Therapy—An Official Publication of the International Society for Antiviral Research, 15(7):935-950 (2010).

(56) References Cited

OTHER PUBLICATIONS

Bordone et al., "Calorie restriction, SIRT1 and metabolism: understanding longevity," Nat Rev Mol Cell Biol, 6:298-305 (2005).
Borradaile et al., "NAD+, Sirtuins, and Cardiovascular Disease," Current Pharmaceutical Design, 15(1):110-117 (2016).
Brittain et al., "X-Ray Diffraction of Pharmaceutical Materials," Profiles of Drug Substances, Excipients, and Related Methodology, 30:273-319 (2003).
Byrn et al., "Pharmaceutical solids: a strategic approach to regulatory considerations," Pharmaceut Res, 12(7):945-954 (1995).
Caira., Crystalline Polymorphism of Organic Compounds, Topics in Current Chemistry, 198: 163-208 (1998).
Cardiac Medications, Heart.org, http://www.heart.org/en/health-topics/heart-attack/treatment-of-a-heart-attack/cardiac-medications (2015).
CAS Registry No. 108273-23-0 (1987).
CAS Registry No. 108489-22-1 (1987).
CAS Registry No. 1094-61-7 (1984).
CAS Registry No. 150035-58-8 (1993).
CAS Registry No. 906748-40-1 (2006).
Cattaneo-Pangrazzi ., "The novel heterodinucleoside dimer 5-FdU-NOAC is a potent cytotoxic drug and a p53-independent inducer of apoptosis in the androgen-independent human prostate cancer cell lines PC-3 and DU-145", The Prostate 45(1): 8-18 (2000).
Cayman Chemical, "beta-Nicotinamide mononucleotide," Item No. 16411 Product Information (2014).
Cayman Chemical, β-Nicotinamide Mononucleotide, Item No. 16411 Safety Data Sheet, Cayman Chemical (2015).
Chemical Cayman, "Nicotinic Acid Mononucleotide," Item No. 32883.
Cherney, "Osteoarthritis Medications List," Healthline, https://www.healthline.com/health/osteoarthritis/medications-list#nsaids (2016).
Cho et al., "Efficient synthesis of nucleoside aryloxy phosphoramidate prodrugs utilizing benzyloxycarbonyl protection," Tetrahedron, 67(30): 14 pages (2011).
Congiatu et al., "Novel potential anticancer naphthyl phosphoramidates of BVdU: separation of diastereoisomers and assignment of the absolute configuration of the phosphorus center," Journal of medicinal chemistry, 49(2): 452-455 (2006).
Corda et al., "Functional aspects of protein mono-ADP-ribosylation," EMBO J, 22(9):1953- 1958 (2003).
Cross et al., "Rules for the Nomenclature of Organic Chemistry. Section E: Sterohemistry," Pure Appl Chem, 45(1):11-30, (1976).
Database Registry Chemical Abstracts, Database Accession No. 807266-77-9, CAS Registry No. 807266-77-9 (Jan. 2, 2005).
Dekker, Polymorphism in Pharmaceutical Solids, First Ed, pp. 184-208 (1999).
Dekker, Polymorphism in Pharmaceutical Solids, First Ed, pp. 7-8 (1999).
Diabetes Treatment, Drugs.com, https://www.drugs.com/diabetes-treatment.html (2018).
Dowden et al., "Chemical Synthesis of the Novel CA 2+ Messenger NAADP," Nucleosides, Nucleotides and Nucleic Acids, 24(5-7):513-518 (2005).
Erion et al., "Design, Synthesis, and Characterization of a Series of Cytochrome P450 3A-Activated Prodrugs (HepDirect Prodrugs) Useful for Targeting Phosph(on)ate-Based Drugs to the Liver," JACS Articles, 126: 5154-5163 (2004).
Extended European Search Report for EP Application No. 16833957.0 dated Dec. 21, 2018.
Extended European Search Report received for EP Patent Application No. EP 16852711. dated Feb. 11, 2019.
Fang et al., "Defective Mitophagy in XPA via PARP-1 Hyperactivation and NAD+/SIRT1 Reduction," Cell, 157(4):882-896 (2014).
Garten et al., "Nampt: Linking NAD biology, metabolism, and cancer," Trends Endocrinol Metab, 20(3):130-138 (2009).
Gavande et al., "DNA repair targeted therapy: The past or future of cancer treatment ?." Pharmacology & Therapeutics, 160:65-83 (2016).
Gockel et al., "Synthesis of an oligonucleotide with a nicotinamide mononucleotide residue and its molecular recognition in DNA helices," Organic & Biomolecular Chemistry, 13(41):10303- 10309 (2015).
Gomes et al., "Declining NAD+ Induces a Pseudohypoxic State Disrupting Nuclear-Mitochondrial Communication druing Aging," Cell, 155(7):1624-1638 (2013).
Guest et al., "Changes in Oxidative Damage, Inflammation and [NAD(H)] with Age in Cerebrospinal Fluid," PLOS One, 9(1):e85335 (2014).
Harrison et al., "Inhibition of Platelet Aggregation and the Platelet Release Reaction by alpha, omega Diadenosine polyphosphates," FEBS Letts 54(1):57-60 (1975).
Hecker et al., "Prodrugs of Phosphates and Phosphonates," Journal of Medicinal Chemistry, 51(8):2328-2345 (2008).
Hirayama, Yuukikagoubutsu Kessyo sakusei Handbook—Genri to Know-how- (Handbook for Preparation of Crystals of Organic Compounds -Principle and Know-how-), Maruzen Co. Ltd., pp. 37-84 (2008).
Huang et al., "Metabolomics-driven identification of adenosine deaminase as therapeutic target in a mouse model of Parkinson's disease," Journal of Neurochemistry, 150: 282-295 (2019).
Imai et al., "NAD+ and sirtuins in aging and disease," Trends in Cell Biol, 24(8):464-471 (2014).
Imai et al., "Transcriptional silencing and longevity protein Sir2 is an NAD-dependent histone deacetylase," Nature, 403:795-800 (2000).
International Search Report and Written Opinion for International Application No. PCT/US2016/045855 dated Nov. 14, 2016.
International Search Report and Written Opinion for International Application No. PCT/US2016/054776 dated Jan. 25, 2017.
International Search Report and Written Opinion for International Application No. PCT/US2019/015672 dated May 15, 2019.
International Search Report and Written Opinion for International Application No. PCT/US2020/023318 dated Jun. 24, 2020.
International Search Report and Written Opinion for International Application No. PCT/US22/031124 dated Oct. 6, 2022.
Invitation to Pay Additional Fees for International Application No. PCT/US22/31124 dated Aug. 5, 2022.
Kamel et al., "Pharmaceutical significance of cellulose: A review", Express Polym Letters 2(11): 758-778 (2008).
Kohsaka et al., "high-Fat Diet Disrupts Behavioral and Molecular Circadian Rhythms in Mice," Cell Metab, 6:414 (2007).
Lee et al., "A Chemical Synthesis of Nicotinamide Adenine Dinucleotide (NAD+)," Chemical Communications (Cambridge), 8: 729-730 (1999).
Lee, "A practical guide to pharmaceutical polymorph screening & selection," Asian Journal of Pharmaceutical Science 9(4):163-175 (2014).
Leisvuori et al. "5', 5'-Phosphodiesters and esterase labile triesters of 2'-C methylribonucleosides", ARKIVOC: Online Journal of Organic Chemistry (2012).
Lin et al., "Nicotinamide adenine dinucleotide, a metabolic regulator of transcription, longevity and disease," Curr Opin Cell Biol, 15:241-246 (2003).
Liu et al., "A Novel Preparation of Nicotinamide Mononucleotide," Nucleosides & Nucleotides, 13(5): 1215-1216 (1994).
Liu et al., "Enzymatic synthesis of polymers containing nicotinamide mononucleotide," Nucleic Acids Research, 23(18):3742 (1995).
Liu et al., "Synthesis of Phosphodiester-type Nicotinamide Adenine Dinucleotide Analogs," Tetrahedron, 65(40): 8378-8383 (2009).
Makarov et al., "Syntheses and chemical properties of B-nicotinamide riboside and its analogues and derivatives," Beilstein J Org Chem, 15: 401-430 (2019).
McGuigan et al., "Certain phosphoramidate derivatives of dideoxy uridine (ddU) are active against HIV and successfully by-pass thymidine kinase," FEBS Letters, 351: 11-14 (1994).
McGuigan et al., "Phosphorodiamidates as a Promising New Phosphate Prodrug Motif for Antiviral Drug Discovery: Application to Anti-HCV Agents," Journal of Medicinal Chemistry, 54: 8632-8645 (2011).
Medications for Dermatitis, Drugs.com, https://www.drugs.com/condition/dermatitis.html (2018).

(56) References Cited

OTHER PUBLICATIONS

Medications for Obesity, Drugs.com, https://www.drugs.com/condition/obesity.html (2018).
Medications for Peripheral Neuropathy, Drugs.com, https://www.drugs.com/condition/peripheral-neuropathy.html (2018).
Medications for Thrombotic/Thromboembolic Disorder, Drugs.com, https://www.drugs.com/condition/thrombotic-thromboembolic-disorder.html (2018).
Menissier de Murcia et al., "Functional Interaction between PARP-1 and PARP-2 in chromosome stability and embryonic development in mouse," EMBO J, 22(9):2255-2263 (2003).
Migaud et al., "Probing Aplysia californica Adenosine 5'-Diphosphate Ribosyl Cyclase for Substrate Binding Requirements: Design of Potent Inhibitors," Biochemistry, 38:9105-9114 (1999).
Mikhailopulo et al., "Synthesis of glycosides of nicotinamide and nicotinamide mononucleotide," Synthesis, 5:388-389 (1981).
Moazed, "Enzymatic activities of Sir2 and chromatin silencing," Curr Opin Cell Biol, 13(2):232-238 (2001).
Montgomery et al., "Synthesis of Potential Anticancer Agents. XXVIII. Simple Esters of 6-Mercaptopurine Ribonucleotide2," The Journal of Organic Chemistry, 26(6):1929-1933 (1961).
Moynihan et al., "Increased dosage of mammalian Sir2 in pancreatic B cells enhances glucose-stimulated insulin secretion in mice," Cell Metab, 2:105-117 (2005).
Nakahata et al., "The NAD+-Dependent Deacetylase SIRT1 Modulates CLOCK-Mediated Chromatin Remodeling and circadian Control," Cell, 134(2):329 (2008).
Nakai et al., Shin Seizaigaku (New Pharmacy), Nanzando Co. Ltd., 1st Edition, 2nd Printing, pp. 102-104, 217-236 (1984).
Nikiforov et al., "Pathways and Subcellular Compartmentation of NAD Biosynthesis in Human Cells," The Journal of Biological Chemistry, 286 (24): 21767-21778 (2011).
Park et al., "Nicotinamide Ribose 5'-0-[S-(3-Bromo-2-oxopropyl)] thiophosphate: A New Affinity Label for NMN Sites in Enzymes," Archives of Biochemistry and Biophysics, 303(2):483-488 (1993).
Pertusati et al., "Medicinal chemistry of nucleoside phosphonate prodrugs for antiviral therapy," Antivir Chem Chemother, 22(5):181-203 (2012).
Petrelli et al., "NMN/NaMN Adenylyltransferase (NMNAT) and NAD Kinase (NADK) Inhibitors: Chemistry and Potential Therapeutic Applications," Current Medicinal Chemistry, 18: 1973-1992 (2011).
Pfleiderer et al., "The mechanism of action of dehydrogenases. V. The adenosine diphosphate residue in nicotinamide-adenine dinucleotide (NAD)" Biochimica et Biophysica Acta, Specialized Section on Enzymological Subjects, 73(1): 39-49 (1963).
Pfleiderer et al., "Zum Wirkungsmechanismus von Dehydrogenasen V. Uber die Bedeutung des Adenosindiphosphatrestes im Nicotinamid-Adenin-Dinucleotid," Biochimica et Biophysica Acta, 73:39-49 (1963).
Pfleiderer et al., "Zum Wirkungsmechanismus von Dehydrogenasen. Das Reaktionsverhalten von Pyridinnucleotiden (PN) und PN-Modellen mit Sulfit als nucleophilem Agens," Chemische Berichte, 93(12):3083-3099 (1960).
Picard et al., "Sirt1 promotes fat mobilization in white adipocytes by repressing PPAR-y," Nature, 429:771-776 (2004).
Preitner et al., "The Orphan Nuclear Receptor REV-ERBa Controls Circadian Transcription within the Positive Limb of the Mammalian circadian Oscillator," Cell, 110:251 (2002).
PubChem SID: 347731451 "Substance Record 321-02-8" retrieved online <https://pubchem.ncbi.nlm.nih.gov/substance/347731451>: 6 pages (Create Date Oct. 23, 2017).
Rajman et al., "Therapeutic Potential of NAD-Boosting Molecules: The In Vivo Evidence," Cell Metabolism, 27(3): 529-547 (2018).
Ramsey et al., "Cicadian clock feedback cycle through NAMPT-mediated NAD+ biosynthesis," Science, 324(5927):651-654 (2009).
Redpath et al., "Nicotinamide Benzimidazolide Dinucleotides Non-Cyclisable Analogues of NAD+," Synlett, 25:2331-2336 (2014).
Riemschneider et al., "Zur Beeinflussung von Stoffwechselvorgangen durch unphysiologische Verbindungen, IV: Nicotinylaminosaureester und Nucleosid-Deritvate," Insect repellent science, 41(3):99-106 (1976).
Rodgers et al., "Nutrient control of glucose homeostasis through a complex of PGC-1α and SIRT1," Nature, 434:113-118 (2005).
Rodionova et al., "Metabolic and bactericidal effects of targeted suppression of NadD and NadE enzymes in mycobacteria," mBio, 5(1):e00747-13 (2014).
Roskar et al., "Analytical Methods for Quantification of Drug Metabolites in Biological Samples," IntechOpen, Chapter 4:79-126 (2012).
Rudic et al., "BMAL1 and CLOCK, Two Essential Components of the Circadian Clock, Are Involved in Glucose Homeostasis," PLOS Biol, 2:e377 (2004).
Rutter et al., "Regulation of Clock and NPAS2 DNA Binding by the Redox State of NAD Cofactors," Science, 293(5529):510 (2001).
Sarma et al., "Investigations of Inter- and Intramolecular Interactions in Flavin-Adenine Dinucleotide by Proton Magnetic Resonance," Biochemistry, 7(12):4359-4367 (1968).
Sato et al., "A Functional Genomics Strategy Reveals Rora as a Component of the Mammalian Circadian Clock," Neuron, 43:527 (2004).
Sharma et al., "X-ray diffraction: a powerful method of characterizing nanomaterials," Recent Research in Science and Technology, 4:77-79 (2012).
Shioji, Kokei Seizai no Seizo Gijutsu (Manufacture Technology of Solid Tablet), CMC Publishing Co. Ltd., Popular Edition, 1st Printing, pp. 9-14 (2003).
Sleep Disorders: Medications for Circadian Rhythm Disorders, WebMD, https://www.webmd.com/sleep-disorders/circadian-rhythm-disorder-medications#1 (2018).
Smith et al., "A phylogenetically conserved NAD+-dependent protein decetylase activity in the Sir2 protein family," Proc Natl Acad Sci, 97(12):6658-6663 (2000).
Soto-Gamez et al., "Therapeytic interventions for aging: the case of cellular senescence," Drug Discovery Today, 22(5):786-795 (2017).
Stein et al., "Expression of nampt in hippocampal and cortical excitatory neurons is critical for cognitive function," J Neurosci, 34(17): 5800-5815 (2014).
Stein et al., "Scientific ablation on Nampt in adult neural stem cells recapitulates their functional defects during aging." EMBO J, 33(12):1321-1340 (2014).
Stieger et al., "7:Recrystallization of Active Pharmaceutical Ingredients," Crystallization—Science and Technology, 183-204 (2012).
Takada, "API form screening and selection in drug discovery stage", Pharm Stage, 6(10):20-25. (2007).
Takahashi et al., "The Genetics of Mammalian Circadian Order and Disorder: Implications for Physiology and Disease," Nat Rev Genet, 9(10):764 (2008).
The Chemical Society of Japan Ed., 4th Edition Jikken Kagaku Kouza 1 Kihon Sousa I (4th Edition Experimental Chemistry 1 Basic Operation I), Maruzen Co. Ltd., 2nd Printing, pp. 184-186 (1996).
Thorpe et al., "Lipoamide Dehydrogenase from Pig Heart. Pyridine Nucleotide Induced Changes in Monoalkylated Two-Electron Reduced Enzyme," Biochemistry, 20: 1507-1513 (1981).
Turek et al., "Obesity and Metabolic Syndrome in Circadian Clock Mutant Mice," Science, 308:1043 (2005).
United States Department of Health and Human Services. "Guidance for Industry Pyrogen and Endotoxin Testing: Questions and Answers," pp. 1-10 (2012).
United States Pharmacopeia General Chapter <151> Pyrogen Test, 2 pages.
Walt et al., "An Efficient Chemical and Enzymatic Synthesis of Nicotinamide Adenine Dinucleotide (NAD+)," Journal of the American Chemical Society, 106(1): 234-239 (1984).
Wang et al., "A local mechanism mediates NAD-dependent protection of axon degeneration," J Cell Biol, 170(3):349-355 (2005).
Wiemer et al., "Prodrugs of Phosphnates and Phosphates: Crossing the Membrane Barrier," Topics in Current Chemistry, 360:115-160 (2014).

(56) References Cited

OTHER PUBLICATIONS

Woenckhaus, "Synthesen und biochemische Eigenschaften wassertoffubertragender Coenzye modelle," Chemische Berichte, 97(9):2439-2446 (1964).
Wound Care Medications, GoodRx.com, https://www.goodrx.com/wound-care/drugs (2018).
Yang et al., "NAD+-dependent Deacetylase SIRT3 Regulates Mitochondrial Protein Synthesis by Deacetylation of the Ribosomal Protein MRPL10," J Biol Chem, 285: 7417-7429 (2010).
Yoshino et al., "Nicotinamide Mononucleotide, a Key NAD+ Intermediate, Treats the Pathology of Diet- and Age-Induced Diabetes in Mice," Cell Metab, 14(4): 528-536 (2011).
Pencina et al., "MIB-626, an Oral Formulation of a Microcrystalline Unique Polymorph of Beta-Nicotinamide Mononucleotide, Increases Circulating Nicotinamide Adenine Dinucleotide and its Metabolome in Middle-Aged and Older Adults", J Gerontol A Biol Sci Med Sci, 2023, vol. 78, No. 1, 90-96.
Pencina et al., "Nicotinamide Adenine Dinucleotide Augmentation in Overweight or Obese Middle-Aged and Older Adults: A Physiologic Study", The Journal of Clinical Endocrinology & Metabolism, Feb. 6, 2023, 00, pp. 1-13.
Galli et al., "The Nicotinamide Phosphoribosyltransferase: A Molecular Link between Metabolism, Inflammation, and Cancer". Cancer Research, 70(1), pp. 8-11, 2010.

\* cited by examiner

CRYSTALLINE SOLIDS OF NICOTINIC ACID MONONUCLEOTIDE AND ESTERS THEREOF AND METHODS OF MAKING AND USE

CROSS-REFERENCE TO RELATED APPLICATIONS

This application is a continuation of International Application No. PCT/US22/31124, filed May 26, 2022, which claims priority to U.S. Provisional Application No. 63/193,905, filed May 27, 2021, each of which is incorporated herein by reference in its entirety for all purposes.

BACKGROUND

Nicotinamide adenine dinucleotide (NAD) and related compounds are known as essential coenzymes in cellular redox reactions in all living organisms. Several lines of evidence have also shown that NAD participates in a number of important signaling pathways in mammalian cells, including poly(ADP-ribosyl)ation in DNA repair, mono-ADP-ribosylation in the immune response and G protein-coupled signaling, and the synthesis of cyclic ADP-ribose and nicotinate adenine dinucleotide phosphate (NAADP) in intracellular calcium signaling. It has also been shown that NAD and its metabolites play an important role in transcriptional regulation. In particular, the discovery of Sir2 NAD-dependent deacetylase activity drew attention to this role of NAD. Despite the advances in understanding the biology of NAD, there remains a need for improved compositions and methods of using such compositions for pharmacologic intervention and/or manipulation of the NAD pathway in living cells and tissues.

Nicotinic acid mononucleotide (also known as nicotinate ribonucleotide) and certain nicotinate mononucleotide derivates are believed to increase cellular NAD production (Sauve, U.S. Pat. No. 10,961,268 B2). However, these compounds are difficult to synthesize in a pharmaceutically appropriate scale with sufficient purity. Given the therapeutic benefits associated with nicotinic acid mononucleotide and its derivatives, there is a need for improved compositions and methods for preparing such compositions.

SUMMARY

The present disclosure relates to compounds, crystalline solids, and compositions of compounds and/or crystalline solids for modulation of nicotinamide adenine dinucleotide (NAD, also referred to as NAD+ in its oxidized form and NADH in its reduced form).

One aspect of the disclosure relates to a crystalline solid comprising a compound of Formula (I),

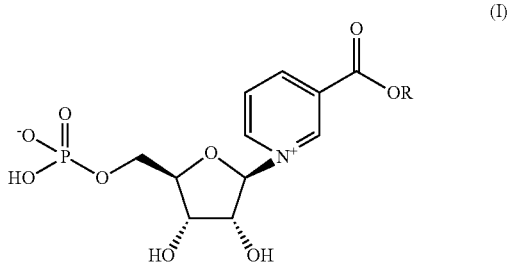

(I)

wherein R is n-propyl (Compound 1).

A further aspect of the disclosure relates to a crystalline solid comprising a compound of Formula (II), (II)

In some embodiments, the disclosure relates to methods of making such compounds, crystalline solids, and compositions, as well as compounds and compositions of Formula (I) wherein R is C1-C4 alkyl or C2-C4 alkenyl. In some embodiments, the disclosure relates to pharmaceutical compositions containing one or more NAD modulating compounds and/or crystalline solids as a first ingredient in combination with one or more active pharmaceutical ingredients. In further embodiments, the disclosure relates to methods of using such compounds, crystalline solids, and/or compositions to promote the increase of intracellular levels of nicotinamide adenine dinucleotide (NAD) in cells and tissues for treating diseases and/or improving cell and tissue survival.

DETAILED DESCRIPTION

Definitions

Figure 1A:
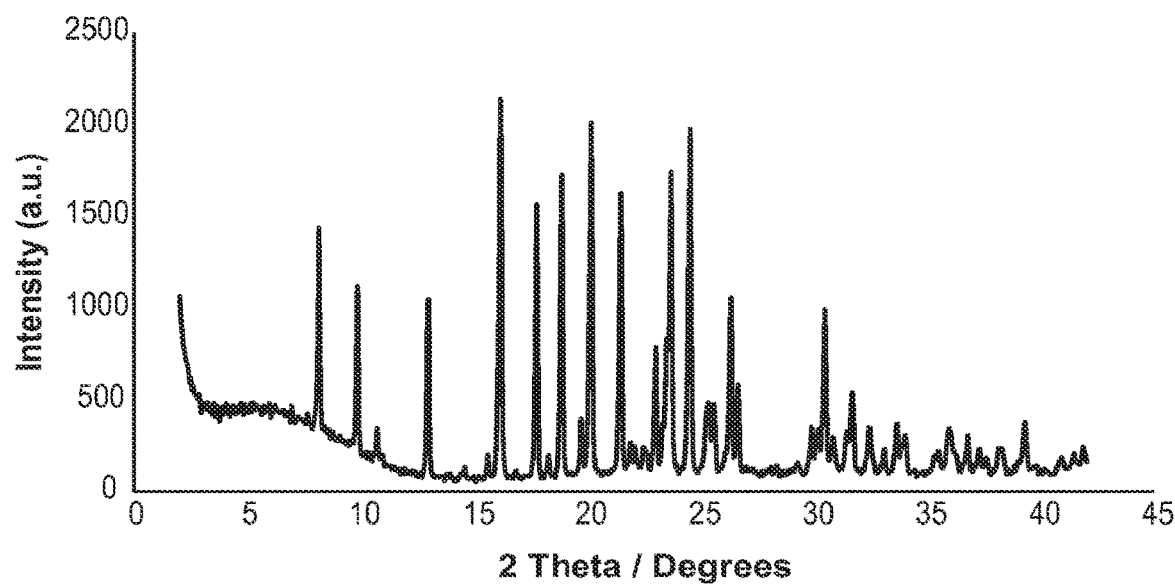
FIG. 1A shows an experimentally obtained XRD pattern of Compound 1 as a crystalline solid.

Unless defined otherwise, all technical and scientific terms used herein have the meaning commonly understood by a person skilled in the art of the present disclosure. As used herein, the following terms have the meanings ascribed to them below, unless specified otherwise.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

Ranges provided herein are understood to be shorthand for all of the values within the range. For example, a range of 1 to 50 is understood to include any number, combination of numbers, or sub-range from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The term "alkyl" as used herein is a branched or unbranched saturated hydrocarbon group of from 1 to about 20 carbon atoms, preferably from 1 to about 10 carbon atoms. Examples of straight chained and branched alkyl groups include methyl, ethyl, n-propyl, iso-propyl, n-butyl, sec-butyl, tert-butyl, pentyl, hexyl, pentyl and octyl. The alkyl group can be cyclic or acyclic. The alkyl group can be branched or unbranched (i.e., linear). A "lower alkyl" group is an alkyl group containing from one to six (e.g., from one to four) carbon atoms.

The term "alkenyl", as used herein, refers to an aliphatic group containing at least one double bond.

The terms "optional" or "optionally" as used herein means that a subsequently described event or circumstance may but need not occur, and that the description includes instances where the event or circumstance occurs and instances in which it does not. For example, "optional bond" means that the bond may or may not be present, and that the description includes single, double, or triple bonds.

The term "purified," as described herein, refers to the purity of a given compound. For example, a compound is "purified" when the given compound is a major component of the composition, i.e., at least about 50% w/w pure. Thus, "purified" embraces at least about 50% w/w purity, at least about 60% w/w purity, at least about 70% purity, at least about 80% purity, at least about 85% purity, at least about 90% purity, at least about 92% purity, at least about 94% purity, at least about 96% purity, at least about 97% purity, at least about 98% purity, at least about 99% purity, at least about 99.5% purity, and at least about 99.9% purity, wherein "substantially pure" embraces at least about 97% purity, at least about 98% purity, at least about 99% purity, at least about 99.5% purity, and at least about 99.9% purity.

The term "metabolite," as described herein, refers to a compound produced in vivo after administration to a subject.

The term "salts," as described herein, refers to a compound comprising a cation and an anion, which can be produced by the protonation of a proton-accepting moiety and/or deprotonation of a proton-donating moiety. It should be noted that protonation of the proton-accepting moiety results in the formation of a cationic species in which the charge is balanced by the presence of a physiological anion, whereas deprotonation of the proton-donating moiety results in the formation of an anionic species in which the charge is balanced by the presence of a physiological cation.

The phrase "pharmaceutically acceptable salt" means a salt that is pharmaceutically acceptable. Examples of pharmaceutically acceptable salts include, but are not limited to: (1) acid addition salts, formed with inorganic acids such as hydrochloric acid, hydrobromic acid, sulfuric acid, nitric acid, phosphoric acid, and the like; or formed with organic acids such as acetic acid, glycolic acid, pyruvic acid, lactic acid, malonic acid, malic acid, maleic acid, fumaric acid, tartaric acid, citric acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, lauryl sulfuric acid, gluconic acid, glutamic acid, salicylic acid, muconic acid, and the like or (2) basic addition salts formed with the conjugate bases of any of the inorganic acids listed above, wherein the conjugate bases comprise a cationic component selected from among $Na^+$, $K^+$, $Mg^{2+}$, $Ca^{2+}$, $NH_gR_{4-g}^+$, in which R is a $C_{1-3}$ alkyl and g is a number selected from 0, 1, 2, 3, or 4. It should be understood that all references to pharmaceutically acceptable salts include solvent addition forms (solvates) or crystalline solids as defined herein, of the same acid addition salt.

The present disclosure also includes useful forms of the compounds of the present disclosure, such as metabolites, solvates, prodrugs, salts, in particular pharmaceutically acceptable salts, and/or co-precipitates.

The compounds of the present disclosure can exist as solvates, wherein the compounds of the present disclosure form a crystal that contains molecules of polar solvents, such as water, methanol or ethanol, for example, as structural element of the crystal lattice of the compounds. The molecules of polar solvents may be present in a stoichiometric or non-stoichiometric ratio with the molecules of the compound. In the case of stoichiometric solvates, e.g., a hemi-, (semi-), mono-, sesqui-, di-, tri-, tetra-, penta- etc. solvates, respectively, are possible. The present disclosure includes all such solvates.

Further, it is possible for the compounds of the present disclosure to exist in free form, e.g., as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present disclosure.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

The terms "treatment", "treating", "palliating" and "ameliorating" are used interchangeably herein. These terms refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compounds and/or compositions can be administered to a patient at risk of developing a particular disease, or to a patient reporting one or more of the physiological symptoms of a disease, even though a diagnosis of this disease may not have been made.

As used herein, a therapeutic that "prevents" a disorder or condition refers to a compound and/or crystalline solid thereof that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the subject of one or more of the disclosed compositions. If it is administered prior to clinical manifestation of the unwanted condition (e.g., disease or other unwanted state of the subject) then the treatment is prophylactic (i.e., it protects the subject against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "preparation" or "dosage form" is intended to include both solid and liquid formulations of the active compound and/or crystalline solid thereof, and one skilled in the art will appreciate that an active ingredient can exist in different preparations depending on the desired dose and pharmacokinetic parameters.

The term "excipient" as used herein refers to a compound that is used to prepare a pharmaceutical composition, and is generally safe, non-toxic and neither biologically nor otherwise undesirable, and includes excipients that are acceptable for veterinary use as well as human pharmaceutical use.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

The recitation of a listing of elements in any definition of a variable herein includes definitions of that variable as any single element or combination (or sub-combination) of listed elements. The recitation of an embodiment herein includes that embodiment as any single embodiment or in combination with any other embodiments or portions thereof.

It is to be understood that wherever values and ranges are provided herein, all values and ranges encompassed by these values and ranges are meant to be encompassed within the scope of the present disclosure. Moreover, all values that fall within these ranges, as well as the upper or lower limits of a range of values, are also contemplated by the present application.

Compounds and Crystalline Solids

In one aspect, the disclosure provides a crystalline solid comprising a compound of Formula (I),

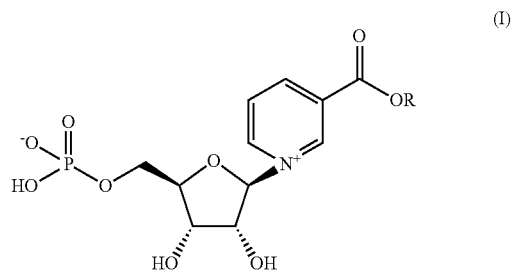

wherein R is n-propyl. The compound of Formula (I), wherein R is n-propyl, is alternatively referred to herein as "Compound 1."

In some embodiments, the crystalline solids described herein are characterized by X-ray diffraction (XRD). In certain embodiments, the XRD is X-ray powder diffraction (XRPD). θ represents the diffraction angle, measured in degrees. In some embodiments, the diffractometer used in XRD measures the diffraction angle as two times the diffraction angle θ. Thus, in certain embodiments, the diffraction patterns described herein refer to X-ray intensity measured against angle 2θ.

Figure 1B:
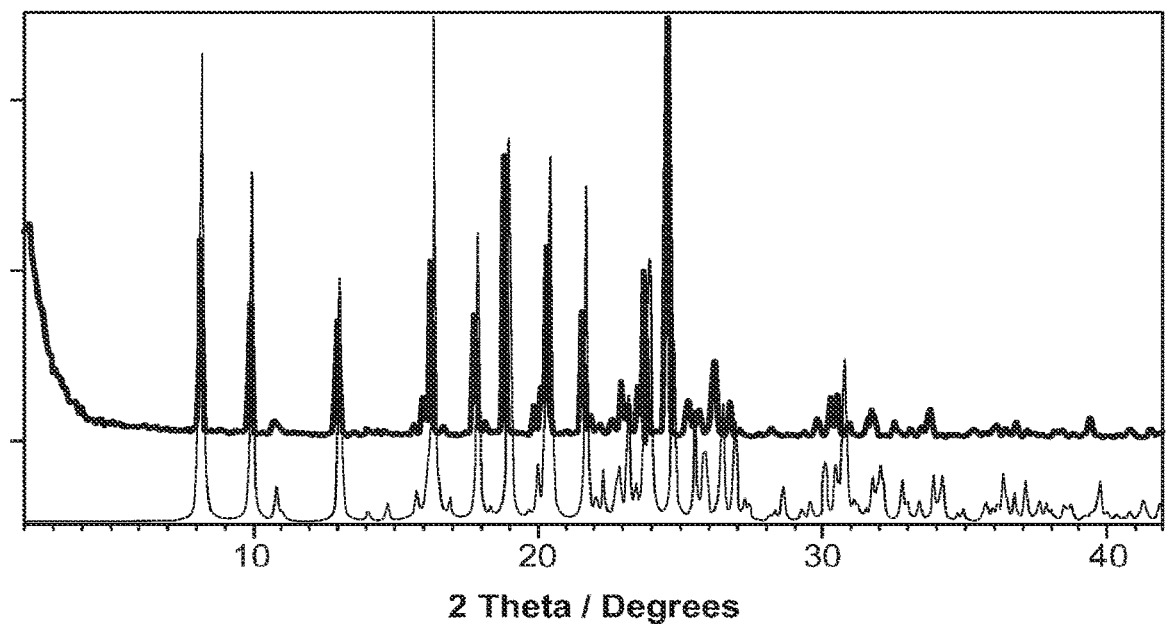
FIG. 1B shows an overlay where the top pattern is an experimental diffractogram for Compound 1 at room temperature; and the bottom pattern is the calculated diffractogram for Compound 1 simulated at 100 K degrees. Slight differences in the simulated and experimental diffractograms are attributable to lattice variations with temperature and preferred orientation.
Figure 1C:
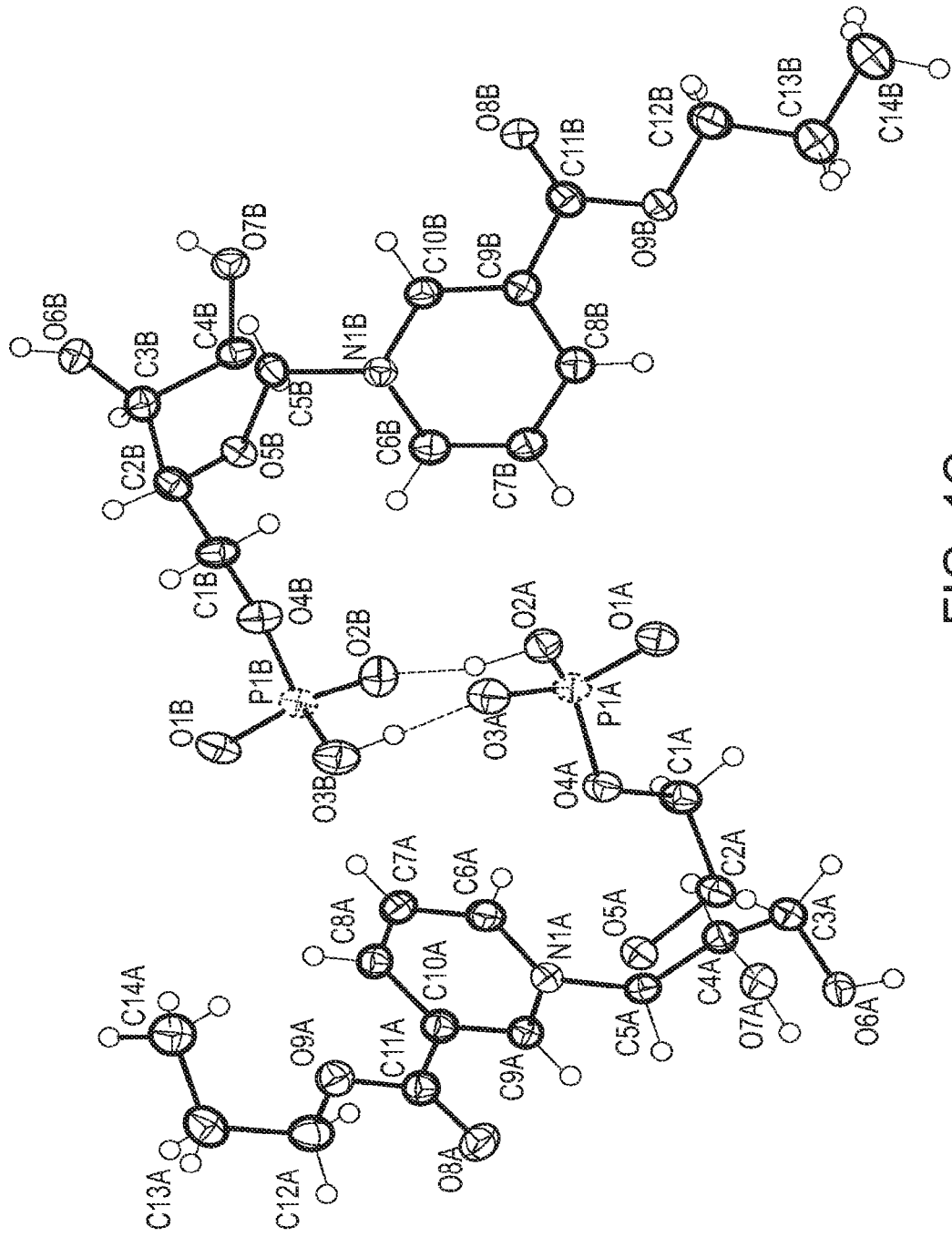
FIG. 1C is a representation of a crystal lattice unit cell for Compound 1.

In some embodiments, the crystalline solid comprising a compound of Formula (I) has 2θ values of 16.1, 20.1, and 24.5. In some embodiments, the crystalline solid comprising a compound of Formula (I) has 2θ values of 16.1, 20.1, 24.5, 23.7, 18.8, 21.5, 17.7, 8.1, 9.9, 13.0, 26.3, and 30.4. In some embodiments, the crystalline solid comprising a compound of Formula (I) has 2θ values of 16.1, 20.1, 24.5, 23.7, 18.8, 21.5, 17.7, 8.1, 9.9, 13.0, 26.3, 30.4, 23.0, 26.6, 25.3, 25.5, and 19.7. In some embodiments, the crystalline solid comprising a compound of Formula (I) has an XRD pattern substantially as shown in FIG. 1 (A or B). In some embodiments, the XRD pattern is of a methanol solvate of the compound of Formula (I). In some embodiments, the XRD pattern is a non-solvate of the compound of Formula (I). In some embodiments, the XRD pattern corresponds to a three-dimensional shape corresponding to FIG. 1C.

In certain embodiments, the compound of Formula (I) is not solvated or hydrated in the crystalline solid (e.g., the crystal lattice does not comprise molecules of a solvent or water). In certain embodiments, the crystalline solid comprising a compound of Formula (I) comprises non-hydrated water and/or non-solvated solvent. In certain embodiments, such non-hydrated water and/or non-solvated solvent is present in a residual amount, such as less than 10% by weight, or less than 5% by weight, or in an amount greater than zero but less than 1% by weight.

In certain embodiments, the compound of Formula (I) is solvated by one or more solvents. In certain embodiments, the compound of Formula (I) is solvated by an alcohol to form an alcohol solvate, preferably methanol to form a methanol solvate. In certain embodiments, the crystalline methanol solvate of the compound of Formula (I) contains about 1.0, about 1.1, or about 1.2 molecules of methanol to one molecule of the compound of Formula (I). In certain embodiments, the compound of Formula (I) is solvated by ethanol. In certain embodiments, the compound of Formula (I) is hydrated by water. In certain embodiments, the compound of Formula (I) is solvated/hydrated by ethanol and water. In various embodiments, the crystalline solid is a solvate selected from a methanol solvate, an ethanol solvate, a 1-propanol solvate, a 2-propanol solvate, a C-4 alcohol solvate, a C-5 alcohol solvate, and a C-6 alcohol solvate, preferably the methanol solvate.

In various embodiments, the compound of Formula (I) with an XRD pattern as disclosed herein is prepared from amorphous material of greater than 90% purity, comprising the steps of dissolving the amorphous material in an alcohol, and allowing the product to precipitate over time, preferably at ambient temperature. In various embodiments, the compound of Formula (I) is prepared from amorphous material by a method comprising the steps of dissolving the amorphous material in water or an aqueous solution, then diluting the resulting solution with an anti-solvent, and allowing the compound of Formula (I) to precipitate over time. In various embodiments, the anti-solvent is an alcohol such as ethanol, methanol, propanol, or another alcohol of eight or fewer carbons. In various embodiments, the anti-solvent is ethanol. In various embodiments, the anti-solvent is denatured ethanol.

In one aspect, the disclosure provides a crystalline solid comprising a compound of Formula (II),

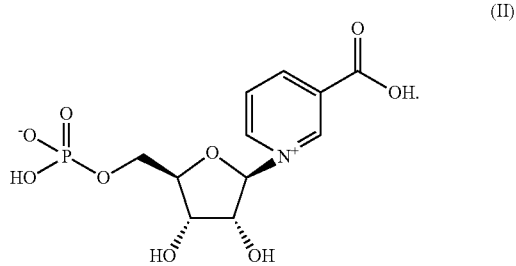

(II)

The compound of Formula (II) is alternatively referred to herein as "Compound 2."

Figure 2A:
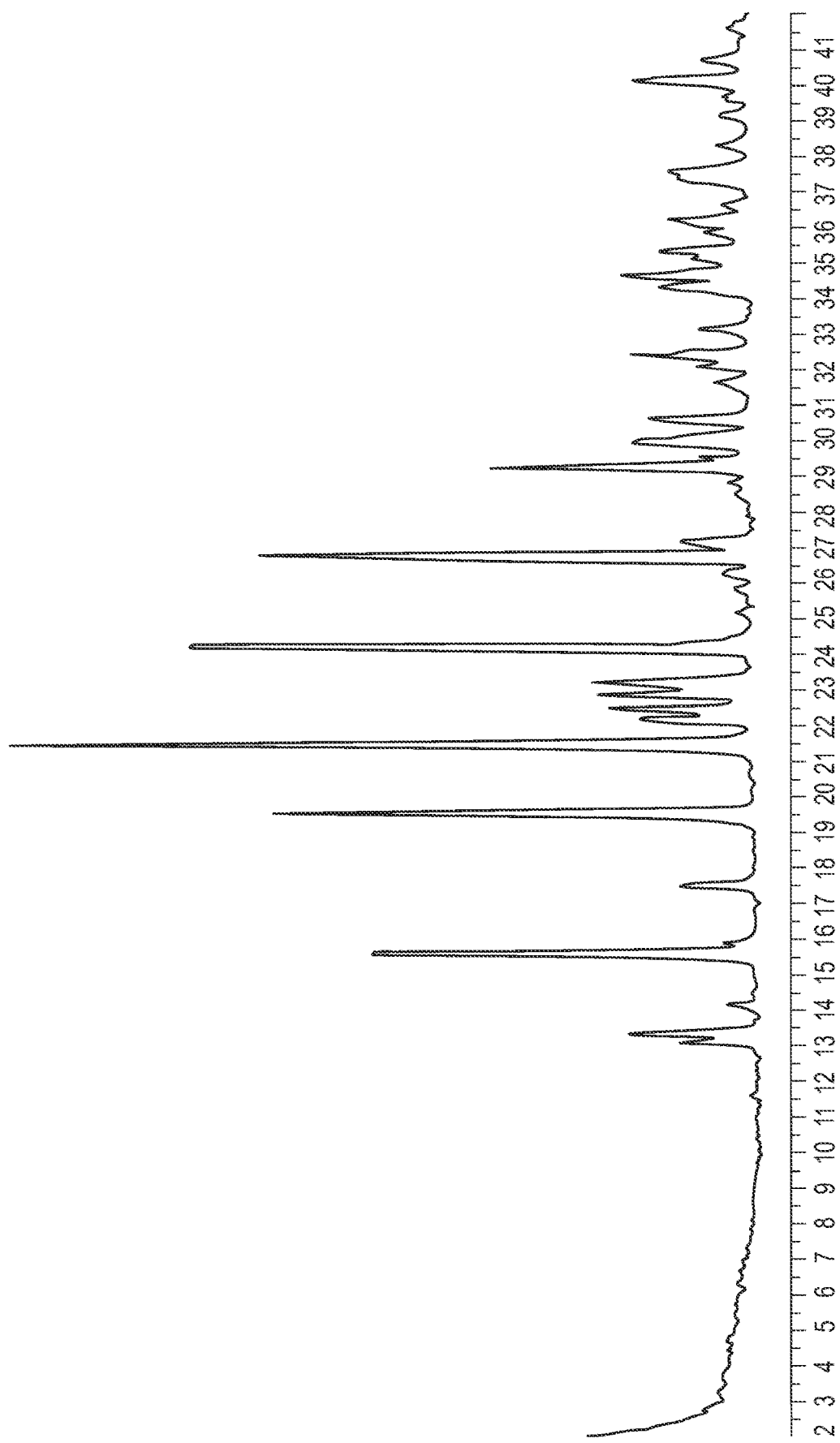
FIG. 2A shows an experimentally obtained XRD pattern of Compound 2 as a crystalline solid.
Figure 2B:
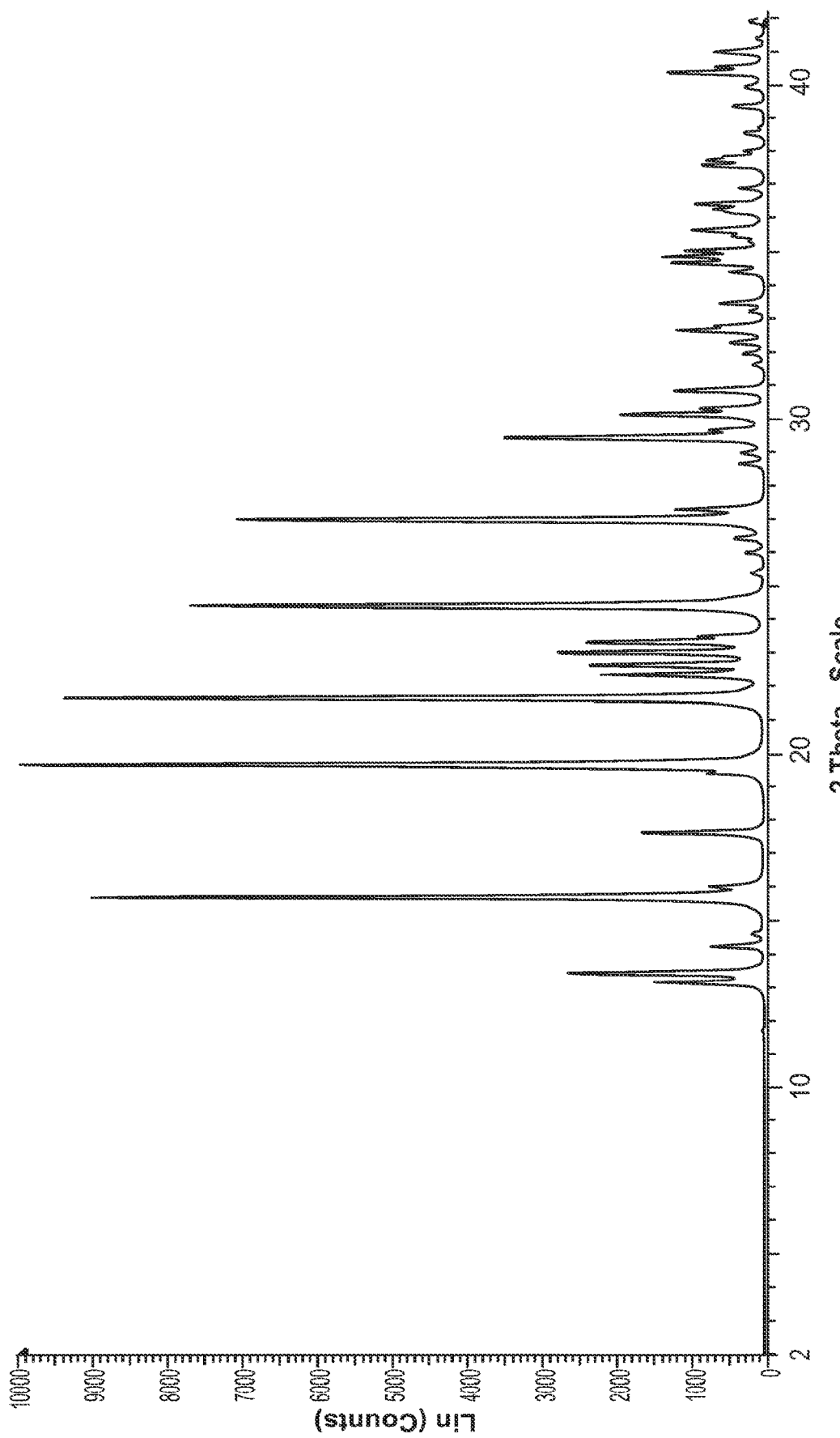
FIG. 2B shows a simulated XRD pattern of Compound 2 as a crystalline solid.

In some embodiments, the crystalline solid comprising a compound of Formula (II) has 2θ values of 21.5, 24.2, 26.7, and 19.6. In some embodiments, the crystalline solid comprising a compound of Formula (II) has 2θ values of 21.5, 24.2, 26.7, 19.6, 15.6, and 29.3. In some embodiments, the crystalline solid comprising a compound of Formula (II) has 2θ values of 21.5, 24.2, 26.7, 19.6, 15.6, 29.3, 22.9, 23.1, 22.5, 13.3, 22.2, 30.0, 30.6, 13.1, 27.2, and 17.5. In some embodiments, the crystalline solid comprising a compound of Formula (II) has an XRD pattern substantially as shown in FIG. 2. In some embodiments, the XRD pattern is of a hydrate of the compound of Formula (II).

In certain embodiments, the compound of Formula (II) is not solvated or hydrated in the crystalline solid (e.g., the crystal lattice does not comprise molecules of a solvent or water). In certain embodiments, the compound of Formula (II) is solvated by one or more solvents. In certain embodiments, the crystalline solid comprising a compound of Formula (II) comprises non-hydrated water and/or non-solvated solvent. In certain embodiments, such non-hydrated water and/or non-solvated solvent is present in a residual amount, such as less than 10% by weight, or less than 5% by weight, or in an amount greater than zero but less than 1% by weight.

In some embodiments, the compound of Formula (II) is solvated by water to form a hydrate. In other embodiments, the compound of Formula (II) is solvated by an alcohol to form an alcohol solvate. In certain embodiments, the crystalline hydrate of the compound of Formula (II) contains about 1.0, about 1.1, or about 1.2 molecules of water to one molecule of the compound of Formula (II). In certain embodiments, the compound of Formula (II) is solvated by ethanol. In certain embodiments, the compound of Formula (II) is hydrated by water. In certain embodiments, the compound of Formula (II) is solvated/hydrated by ethanol and water. In various embodiments, the crystalline solid comprising the compound of Formula (II) is a solvate selected from a methanol solvate, an ethanol solvate, a 1-propanol solvate, a 2-propanol solvate, a C-4 alcohol solvate, a C-5 alcohol solvate, and a C-6 alcohol solvate, preferably the methanol solvate.

In various embodiments, the compound of Formula (II) with an XRD pattern as disclosed herein is prepared from amorphous material of greater than 90% purity, by a method comprising the steps of dissolving the amorphous material in an alcohol, and allowing the compound of Formula (II) to precipitate over time, preferably at ambient temperature. In various embodiments, the compound of Formula (II) is prepared from amorphous material by a method comprising the steps of dissolving the amorphous material in water or an aqueous solution, then diluting the resulting solution with an anti-solvent, and allowing the compound of Formula (II) to precipitate over time. In various embodiments, the anti-solvent is an alcohol such as ethanol, methanol, propanol, or another alcohol of eight or fewer carbons. In various embodiments, the anti-solvent is ethanol. In various embodiments, the anti-solvent is denatured ethanol.

It will be apparent that the compounds of Formula (I) and Formula (II) may exist in various protonation states, depending on, among other things, the pH of their environment. In various pH environments, the compounds of Formula (I) and Formula (II) exist as zwitterions, or internal salts, as drawn herein.

In various embodiments, the compounds of Formula (I) and (II) are one or more salts, wherein said salts are formed with a cation selected from $H^+$, $Li^+$, $Na^+$, $K^+$, $Mg^{2+}$, and $Ca^{2+}$ and/or said salts are formed with an anion selected from acetate, trifluoromethansulfonate (triflate), halide, trifluoroacetate, formate, $H_2PO_4^-$, $HPO_4^{2-}$, $OH^-$, $HSO_4^-$, $SO_4^{2-}$, $NO_3^-$, $HCO_3^-$, and $CO_3^{2-}$, and mixtures thereof. In various embodiments, the compound is a zwitterion.

The present disclosure includes the use of pharmaceutically acceptable salts of compounds of the disclosure and/or crystalline solids thereof. In certain embodiments, contemplated salts of the disclosure include, but are not limited to, alkyl, dialkyl, trialkyl or tetra-alkyl ammonium salts. In certain embodiments, contemplated salts of the disclosure include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts.

In certain embodiments, the compound is a salt with an anion selected from acetate, triflate, halide, trifluoroacetate, or formate. In other embodiments, if the disclosed compound is in contact with a media, e.g., aqueous media, the anion can be selected from, for example, $OH^-$, $H_2PO_4^-$, $HPO_4^{2-}$, $HSO_4^-$, $SO_4^{2-}$, $NO_3^+$, $HCO_3^-$, and $CO_3^{2-}$.

In some embodiments, the disclosed compounds are in the form of a negatively charged phosphate, which may form a salt with any suitable cation. The cation can alter as the compound is isolated or transferred into media with different anionic species. For example, a disclosed compound may be in the form of a phosphate salt that is a pharmaceutically acceptable salt as described herein. In certain embodiments, the cation can be selected from $Li^+$, $Na^+$, $K^+$, $Mg^{2+}$, and $Ca^{2+}$.

In some embodiments, the crystalline solids described herein are not a part of a solution, suspension, mixture, slurry, reaction mixture, or the like.

In some embodiments, the average size of the single crystals of the crystalline solid comprising the compound of Formula (I) or Formula (II) is greater than about 1 micrometer, greater than about 5 micrometers, greater than about 10 micrometers, or greater than about 20 micrometers. In further embodiments, the average size of the single crystals of the crystalline solid comprising the compound of Formula (I) or Formula (II) is about 1 to about 100 micrometers, about 20 to about 100 micrometers, about 1 to about 500 micrometers, about 1 to about 250 micrometers, about 20 to about 250 micrometers, or about 20 to about 500 micrometers.

In some embodiments, the crystalline solids described herein have lower solubility in water compared to amorphous solids of the compounds of Formula (I) and Formula (II). In preferred embodiments, the solubility ratio of the crystalline solid to water is about 1:5 to about 1:75 by weight. In more preferred embodiments, the solubility ratio of the crystalline solid to water is about 1:10 to about 1:60 by weight. This lower solubility in water may impart desirable therapeutic properties.

In various embodiments, the crystalline solid is anhydrous. In various embodiments, the crystalline solid comprises less than about 5% water, less than about 2% water, less than about 1% water, less than about 0.5% water, or less than about 0.1% water. In some embodiments, the percentage is by weight.

In preferred embodiments, the compound of Formula (I) or the crystalline solid thereof comprises less than about 5% impurities, less than about 2% impurities, less than about 1% impurities, or less than about 0.5% impurities. For example, in preferred embodiments, the compound of Formula (I) or the crystalline solid thereof comprises less than about 5% propyl nicotinate, less than about 2% propyl nicotinate, less than about 1% propyl nicotinate, less than about 0.5% propyl nicotinate, or less than about 0.1% propyl nicotinate. In some embodiments, the percentage is by weight.

In preferred embodiments, the compound of Formula (II) or the crystalline solid thereof comprises less than about 5% impurities, less than about 2% impurities, less than about 1% impurities, or less than about 0.5% impurities. For example, in preferred embodiments, the compound of Formula (II) or the crystalline solid thereof comprises less than about 5% nicotinic acid riboside, less than about 2% nicotinic acid riboside, less than about 1% nicotinic acid riboside, less than about 0.5% nicotinic acid riboside, less than about 0.1% nicotinic acid riboside, or less than about 0.01% nicotinic acid riboside. In some embodiments, the percentage is by weight.

In certain preferred embodiments, the crystalline solid comprising the compound of Formula (I) or Formula (II) is pure or substantially pure. In certain preferred embodiments, the crystalline solid is greater than about 90% pure. More preferably, the crystalline solid is greater than about 95% pure, or even more preferably greater than about 98% pure, for example, greater than about 99% pure. In some embodiments, the percentage is by weight. In preferred embodiments, the crystalline solid comprises at least about 90%, at least about 95%, at least about 96%, at least about 97%, at least about 98%, at least about 99%, at least about 99.5%, or at least about 99.9% of the compound of Formula (I) or Formula (II). In some embodiments, the percentage is by weight.

The crystalline solids described herein may have advantageous properties compared to amorphous forms of the compounds of Formula (I) and Formula (II). In some embodiments, the crystalline solids exhibit improved chemical and/or physical stability, for example, at elevated temperatures. In certain embodiments, compositions comprising the crystalline solids exhibit improved chemical and/or physical stability. In some embodiments, the crystalline solids have improved storage stability. In certain embodiments, the crystalline solids exhibit better handling properties in the manufacturing process than amorphous forms, which may result in compounds, crystalline solids, and compositions having higher purity, stability and/or consistency. In some embodiments, the crystalline solids may be easier to process under typical pharmaceutical processing conditions. In certain embodiments, the improved handling properties include improved sticking and flow properties. In some embodiments, the crystalline solids described herein are less hygroscopic compared to amorphous forms. For example, when exposed to a humid environment (e.g., at least 50% humidity), the crystalline solids may take up less water than a corresponding amorphous form would under identical conditions. In certain embodiments, the crystalline solids maintain structural integrity when exposed to humidity, e.g., may be less susceptible to swelling or to conversion to a less stable form. In some embodiments, the crystalline solids described herein have lower solubility and/or dissolution rates compared to amorphous forms. In certain embodiments, in order to prolong the effects of a crystalline solid as a drug, it is desirable to slow the absorption of the crystalline solid. For example, in some embodiments, the crystalline solids described herein are effectively delivered to the intestines and do not significantly dissolve in the stomach. In some embodiments, an extended-release effect is accomplished, for example, by the use of an aqueous suspension of the crystalline solid. In other embodiments, delayed release is accomplished by dissolving or suspending the solid material in an oil vehicle. In some embodiments, the crystalline solids described herein have higher purity than amorphous forms and/or facilitate large-scale preparation of pure material, e.g., at lower cost or with less materialor space-intensive purification methods. In some such embodiments, the crystalline solids and methods described herein facilitate large scale purification, e.g., greater than about 1 gram, greater than about 10 grams, or greater than about 100 grams.

Methods of Preparing the Crystalline Solids

Also provided herein are methods of preparing a crystalline solid of a compound of Formula (I). In certain embodiments, the disclosure relates to a method for preparing a crystalline solid of a compound of Formula (I), comprising a) dissolving the compound of Formula (I) in a solvent to form a mixture; and b) crystallizing the compound of Formula (I) from the mixture to form the crystalline solid.

In preferred embodiments, the mixture comprising the compound of Formula (I) is a solution. In other embodiments, the mixture is a slurry or a suspension. In some embodiments, the solvent is selected from alcohols, ketones, carboxylic acids, esters, ethers, alkanes, water, amines, other liquids of similar polarity and properties, and combinations thereof. In some embodiments, the solvent comprises acetonitrile, N,N-dimethylacetamide (DMA), dimethylformamide (DMF), dimethylsulfoxide (DMSO), methanol, ethanol, ethyl acetate, isopropyl acetate, methanol, methylethyl ketone, N-methyl-2-pyrrolidone (NMP), tetrahydrofuran, a propanol, a butanol, water, or any combination thereof. In certain embodiments, the solvent is a linear or branched alcohol, such as methanol, ethanol, propanol, or butanol, including branched and unbranched isomers thereof. In preferred embodiments, the solvent is methanol. In some embodiments, the solvent comprises two or more of the solvents described herein. In some embodiments, the solution is anhydrous.

In certain embodiments, the temperature of the solvent is above ambient temperature during the dissolving step. In such embodiments, the methods comprise heating the solvent. For example, the temperature of the solvent may be from about 30 to about 50° C. or about 30 to about 40° C., for example, about 35° C. In other embodiments, the temperature of the solvent is about ambient temperature during the dissolving step. In still other embodiments, the temperature of the solvent is below ambient temperature during the dissolving step. In such embodiments, the methods comprise cooling the solvent. In some embodiments, the temperature of the solvent is from about 20 to about 30° C., for example, about 25° C. In preferred embodiments, the compound of Formula (I) is completely dissolved in the solvent before the crystallizing step. By completely dissolved it is meant that the compound occurs in a homogeneous solution rather than a slurry or suspension. In other embodiments, the compound of Formula (I) is partially dissolved in the solvent before the crystallizing step.

In certain embodiments, the methods comprise forming a supersaturated solution from the mixture (e.g., solution) of the compound of Formula (I), wherein the supersaturated solution is supersaturated with respect to the compound of Formula (I). In some embodiments, the supersaturated solution has a supersaturation ratio of about 1 to about 4, for example about 2. In some such embodiments, the compound of Formula (I) is caused to precipitate (e.g., crystallize) from the supersaturated solution. In some embodiments, the resulting precipitate (e.g., crystal) is a crystalline solid described herein.

The supersaturated solution may be formed according to various methods. In some embodiments, forming the supersaturated solution may comprise adding an anti-solvent to the mixture (e.g., solution), lowering the temperature of the mixture (e.g., solution), reducing the volume of the mixture (e.g., solution), or any combination thereof. For example, the methods may comprise adding an anti-solvent, followed by cooling the resulting mixture, followed by adding additional anti-solvent.

In certain embodiments, forming the supersaturated solution comprises lowering the temperature of the mixture comprising the compound of Formula (I). In some such embodiments, the temperature of the solution is lowered to about 0 to about 25° C., about 0 to about 10° C., or about −5 to about 5° C., for example about 0° C. In certain embodiments, allowing the solution to cool may be passive (e.g., allowing the solution to stand at ambient temperature) or active (e.g., cooling the solution in an ice bath or freezer).

In some embodiments, forming the supersaturated solution comprises adding an anti-solvent to the mixture comprising the compound of Formula (I). As used herein, "anti-solvent" means a liquid in which the compounds of Formula (I) and (II) are insoluble, minimally soluble, or partially soluble. In practice, the addition of an anti-solvent to a solution in which the compounds of Formula (I) and (II) are dissolved reduces the solubility of the compounds of Formula (I) and (II) in the solvent, thereby stimulating precipitation.

In certain embodiments, the anti-solvent may be added slowly to prevent uncontrolled crystallization. In some embodiments, the anti-solvent is selected from alcohols, ketones, carboxylic acids, esters, ethers, alkanes, water, amines, other liquids of similar polarity and properties that are miscible with the solvent, and combinations thereof. In some embodiments, the anti-solvent is an alkane solvent, such as a hexane or a pentane solvent, or an aromatic hydrocarbon solvent, such as benzene, toluene, or xylene. In certain embodiments, the anti-solvent is selected from ethyl acetate, isopropyl acetate, methyl tert-butyl ether, methyl isobutyl ketone, tetrahydrofuran, 1-propanol, 2-propanol, ethanol, denatured ethanol, and combinations thereof. In preferred embodiments, the anti-solvent is TBME. In some embodiments, the anti-solvent comprises two or more of the solvents described herein. In some embodiments, the ratio of the solvent to the anti-solvent is about 1:1 to about 8:1 by volume or about 4:1 to about 6:1 by volume, for example about 5:1 by volume.

In certain embodiments, the methods further comprise evaporating the solvent from the mixture. In some embodiments, the solvent may be removed under reduced pressure and/or by heating the solvent such that the solvent evaporates.

In certain embodiments, crystallizing comprises causing secondary nucleation to occur. In some embodiments, crystallizing comprises adding a seed crystal to the solution, wherein the seed crystal comprises the compound of Formula (I). In certain embodiments, the seed crystal is formed during a prior crystallization. In certain such embodiments, the prior crystallization is performed at a smaller scale than the crystallization where the seed crystal is added.

In other embodiments, secondary nucleation may be caused by other changes to the environment of the mixture. For example, crystallization may be promoted by environmental changes including but not limited to crystallizer walls, stirring impellers, and sonication.

In preferred embodiments, the methods comprise isolating the crystalline solid, e.g., by filtering the crystals, by decanting fluid from the crystals, or by any other suitable separation technique.

In certain embodiments, the methods comprise washing the crystalline solid comprising the compound of Formula (II), for example, washing the crystalline solid with a solvent or a mixture of one or more of the solvents and/or anti-solvents described herein. In certain embodiments, washing the crystalline solid comprises washing with a liquid selected from the anti-solvent, the solvent, alcohols, ketones, carboxylic acids, esters, ethers, alkanes, water, amines, other liquids of similar polarity and properties, and combinations thereof. In some embodiments, the liquid is selected from acetonitrile; N,N-dimethylacetamide (DMA); dimethylformamide (DMF); dimethylsulfoxide (DMSO); ethyl acetate; isopropyl acetate; methyl ethyl ketone; methyl isobutyl ketone; N-methyl-2-pyrrolidone (NMP); tetrahydrofuran; alcohols such as methanol, ethanol, a propanol, or a butanol; water; alkane solvents, such as pentanes, hexanes, or heptanes; aromatic hydrocarbon solvents, such as benzene, toluene, or xylene; methyl tert-butyl ether; and combinations thereof. In certain embodiments, the solvents and/or anti-solvents are cooled prior to washing. In some embodiments, the methods comprise drying the crystalline solid, for example under reduced pressure and/or by heating the crystalline solid, and/or under a stream of a drying gas, such as nitrogen, argon, or air.

In certain embodiments, the methods of making the crystalline solids remove one or more impurities from the compound of Formula (I). In some embodiments, the methods do not comprise chromatography or lyophilization to purify the compound of Formula (I). In certain such embodiments, the methods described herein are used for purifying the compound of Formula (I), e.g., as a final purification step in the manufacture of the compound of Formula (I).

The methods described herein may provide the benefit of, among other things, removing impurities from the compound of Formula (I). In preferred embodiments, the crystalline solid comprises less than about 5% impurities, less than about 2% impurities, less than about 1% impurities, or less than about 0.5% impurities. In some preferred embodiments, the crystalline solid comprises less than about 5% propyl nicotinate, less than about 2% propyl nicotinate, less than about 1% propyl nicotinate, less than about 0.5% propyl nicotinate, or less than about 0.1% propyl nicotinate. In some embodiments, the percentage is by weight.

In certain preferred embodiments, the crystalline solid comprising the compound of Formula (II) is pure or substantially pure. In certain preferred embodiments, the crystalline solid is greater than about 90% pure. More preferably, the crystalline solid is greater than about 95% pure, or even more preferably greater than about 98% pure. In some embodiments, the percentage is by weight.

In preferred embodiments, the crystalline solid comprises at least about 90%, at least about 95%, at least about 96%, at least about 97%, at least about 98%, at least about 99%, at least about 99.5%, or at least about 99.9% of the compound of Formula (I). In some embodiments, the percentage is by weight.

Another aspect of the present disclosure provides methods of preparing a crystalline solid of a compound of Formula (II). In certain embodiments, the disclosure relates to a method for preparing a crystalline solid of a compound of Formula (II), comprising a) dissolving the compound of Formula (II) in a solvent to form a mixture; and b) crystallizing the compound of Formula (II) from the mixture to form the crystalline solid. In certain embodiments, the method comprises reacting nicotinic acid riboside with a phosphorous-containing group, such as phosphorus oxychloride, to provide the compound of Formula (II), prior to the dissolving and crystallizing steps.

In preferred embodiments, the mixture comprising the compound of Formula (II) is a solution. In other embodiments, the mixture is a slurry or a suspension. In some embodiments, the solvent is selected from alcohols, ketones, carboxylic acids, esters, ethers, alkanes, water, amines, other liquids of similar polarity and properties, and combinations thereof. In some embodiments, the solvent comprises acetonitrile, N,N-dimethylacetamide (DMA), dimethylformamide (DMF), dimethylsulfoxide (DMSO), methanol, ethanol, ethyl acetate, isopropyl acetate, methanol, methylethyl ketone, N-methyl-2-pyrrolidone (NMP), tetrahydrofuran, a propanol, a butanol, water, or any combination thereof. In certain embodiments, the solvent is a linear or branched alcohol, such as methanol, ethanol, propanol, or butanol, including branched and unbranched isomers thereof. In preferred embodiments, the solvent is water. In certain embodiments, the solvent comprises an alcohol, such as 1-propanol. In some embodiments, the solvent comprises two or more of the solvents described herein. In some embodiments, the ratio of the compound of Formula (II) to the solvent is about 1:2 to about 1:4 by weight, for example about 1:3 by weight.

In certain embodiments, the temperature of the solvent is above ambient temperature during the dissolving step. In such embodiments, the methods comprise heating the solvent. For example, the temperature of the solvent may be from about 30 to about 50° C. or about 30 to about 40° C., for example, about 35° C. In other embodiments, the temperature of the solvent is about ambient temperature during the dissolving step. In still other embodiments, the temperature of the solvent is below ambient temperature during the dissolving step. In such embodiments, the methods comprise cooling the solvent. In some embodiments, the temperature of the solvent is from about 20 to about 30° C., for example, about 25° C. In preferred embodiments, the compound of Formula (II) is completely dissolved in the solvent before the crystallizing step. By completely dissolved it is meant that the compound occurs in a homogeneous solution rather than a slurry or suspension. In other embodiments, the compound of Formula (II) is partially dissolved in the solvent before the crystallizing step.

In certain embodiments, the methods comprise forming a supersaturated solution from the mixture (e.g., solution) of the compound of Formula (II), wherein the supersaturated solution is supersaturated with respect to the compound of Formula (II). In some embodiments, the supersaturated solution has a supersaturation ratio of 1 to about 4, for example about 2. In some such embodiments, the compound of Formula (I) is caused to precipitate (e.g., crystallize) from the supersaturated solution. In some embodiments, the resulting precipitate (e.g., crystal) is a crystalline solid described herein.

The supersaturated solution may be formed according to various methods. In some embodiments, forming the supersaturated solution may comprise adding an anti-solvent to the mixture (e.g., solution), lowering the temperature of the mixture (e.g., solution), reducing the volume of the mixture (e.g., solution), or any combination thereof. For example, the methods may comprise adding an anti-solvent, followed by cooling the resulting mixture, followed by adding additional anti-solvent.

In certain embodiments, forming the supersaturated solution comprises lowering the temperature of the mixture comprising the compound of Formula (II). In some such embodiments, the temperature of the solution is lowered to about 0 to about 25° C., about 0 to about 10° C., or about -5 to about 5° C., for example about 0° C. In certain embodiments, allowing the solution to cool may be passive (e.g., allowing the solution to stand at ambient temperature) or active (e.g., cooling the solution in an ice bath or freezer).

In some embodiments, forming the supersaturated solution comprises adding an anti-solvent to the mixture comprising the compound of Formula (II). In certain embodiments, the anti-solvent may be added slowly to prevent uncontrolled crystallization. In some embodiments, the anti-solvent is selected from alcohols, ketones, carboxylic acids, esters, ethers, alkanes, water, amines, other liquids of similar polarity and properties that are miscible with the solvent, and combinations thereof. In some embodiments, the anti-solvent is an alkane solvent, such as a hexane or a pentane solvent, or an aromatic hydrocarbon solvent, such as benzene, toluene, or xylene. In certain embodiments, the anti-solvent is selected from ethyl acetate, isopropyl acetate, methyl tert-butyl ether, methyl isobutyl ketone, tetrahydrofuran, and combinations thereof. In other embodiments, the solvent is a linear or branched alcohol, such as methanol, ethanol, propanol, or butanol, including branched and unbranched isomers thereof. In preferred embodiments, the anti-solvent is 1-propanol. In some embodiments, the anti-solvent comprises two or more of the solvents described herein. In some embodiments, the ratio of the solvent to the anti-solvent is about 1:0 to about 1:2 by volume or about 1:0 to about 6:7 by volume, for example about 6:7 by volume. In certain embodiments, the supersaturated solution is formed without adding an anti-solvent.

In certain embodiments, the methods further comprise evaporating the solvent from the mixture. In some embodiments, the solvent may be removed under reduced pressure and/or by heating the solvent such that the solvent evaporates.

In some embodiments, the methods further comprise adding an acid or base to adjust the pH of the mixture (e.g., solution) to change the protonation state of the compound of Formula (II). In certain embodiments, the base is an amine, such as triethylamine. In some embodiments, the methods further comprise adding a base to the solution. In certain embodiments, the pH of the solution is adjusted to about 2 to about 4, for example, about 3.

In certain embodiments, crystallizing comprises causing secondary nucleation to occur. In some embodiments, crystallizing comprises adding a seed crystal to the solution, wherein the seed crystal comprises the compound of Formula (II). In certain embodiments, the seed crystal is formed during a prior crystallization. In certain such embodiments, the prior crystallization is performed at a smaller scale than the crystallization where the seed crystal is added.

In other embodiments, secondary nucleation may be caused by other changes to the environment of the mixture. For example, crystallization may be promoted by environmental changes including but not limited to crystallizer walls, stirring impellers, and sonication.

In preferred embodiments, the methods comprise isolating the crystalline solid, e.g., by filtering the crystals, by decanting fluid from the crystals, or by any other suitable separation technique.

In certain embodiments, the methods comprise washing the crystalline solid comprising the compound of Formula (II), for example, washing the crystalline solid with a solvent or a mixture of one or more of the solvents and/or anti-solvents described herein. In certain embodiments, washing the crystalline solid comprises washing with a liquid selected from the anti-solvent, the solvent, alcohols, ketones, carboxylic acids, esters, ethers, alkanes, water, amines, other liquids of similar polarity and properties, and combinations thereof. In some embodiments, the liquid is selected from acetonitrile; N,N-dimethylacetamide (DMA); dimethylformamide (DMF); dimethylsulfoxide (DMSO); ethyl acetate; isopropyl acetate; methyl ethyl ketone; methyl isobutyl ketone; N-methyl-2-pyrrolidone (NMP); tetrahydrofuran; alcohols such as methanol, ethanol, a propanol, or a butanol; water; alkane solvents, such as pentanes, hexanes, or heptanes; aromatic hydrocarbon solvents, such as benzene, toluene, or xylene; methyl tert-butyl ether; and combinations thereof. In preferred embodiments, the methods comprise washing the crystalline solid with a 2:1 by volume mixture of 1-propanol to water, optionally followed by washing the crystalline solid with MTBE. In certain embodiments, the solvents and/or anti-solvents are cooled prior to washing. In some embodiments, the methods comprise drying the crystalline solid, for example under reduced pressure and/or by heating the crystalline solid.

In certain embodiments, the methods of making the crystalline solids remove one or more impurities from the compound of Formula (II). In some embodiments, the methods do not comprise chromatography or lyophilization to purify the compound of Formula (II). In certain such embodiments, the methods described herein are used for purifying the compound of Formula (II), e.g., as a final purification step in the manufacture of the compound of Formula (II).

The methods described herein may provide the benefit of, among other things, removing impurities from the compound of Formula (II). In preferred embodiments, the crystalline solid comprises less than about 5% impurities, less than about 2% impurities, less than about 1% impurities, or less than about 0.5% impurities. In some preferred embodiments, the crystalline solid comprises less than about 5% nicotinic acid riboside, less than about 2% nicotinic acid riboside, less than about 1% nicotinic acid riboside, less than about 0.5% nicotinic acid riboside, or less than about 0.1% nicotinic acid riboside. In some embodiments, the percentage is by weight.

In certain preferred embodiments, the crystalline solid comprising the compound of Formula (II) is pure or substantially pure. In certain preferred embodiments, the crystalline solid is greater than about 90% pure. More preferably, the crystalline solid is greater than about 95% pure, or even more preferably greater than about 98% pure. In some embodiments, the percentage is by weight.

In preferred embodiments, the crystalline solid comprises at least about 90%, at least about 95%, at least about 96%, at least about 97%, at least about 98%, at least about 99%, at least about 99.5%, or at least about 99.9% of the compound of Formula (II). In some embodiments, the percentage is by weight.

Synthesis

In various embodiments, the disclosure provides a method of forming a compound of

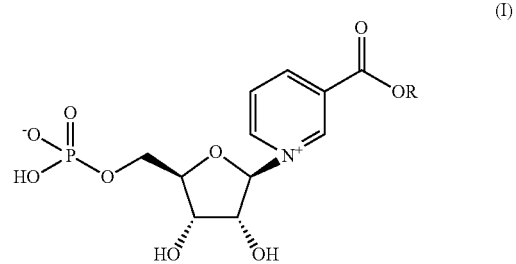

(I)

wherein R is C1-C6 alkyl or C2-C6 alkenyl; the method comprising contacting a compound of Formula (II),

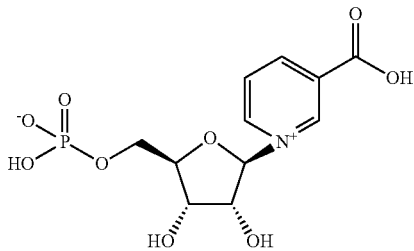

with an alcohol R—OH in the presence of an acid. See, for example, Scheme 1.

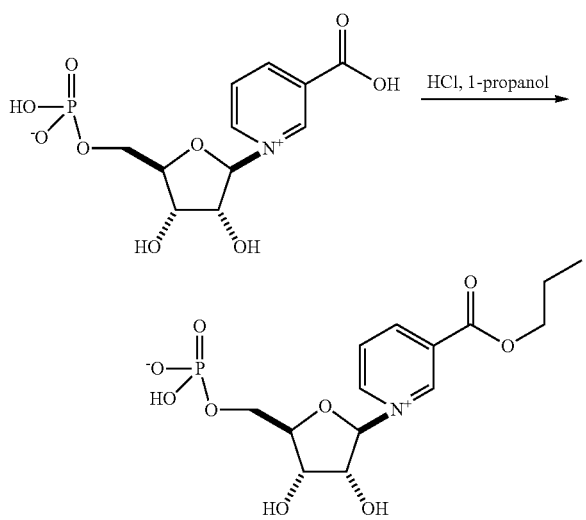

In certain embodiments, R is C1-C6 alkyl. In some embodiments, R is C1-C4 alkyl or C2-C4 alkenyl. In certain embodiments, R is C3 alkyl. In certain embodiments, R is n-propyl.

In some embodiments, the acid is a strong acid. In some embodiments, the acid is an inorganic acid, such as hydrochloric acid, hydrobromic acid, sulfuric acid, nitric acid, phosphoric acid, and the like. In other embodiments, the acid is an organic acid such as glycolic acid, pyruvic acid, lactic acid, malonic acid, malic acid, maleic acid, fumaric acid, tartaric acid, citric acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, lauryl sulfuric acid, gluconic acid, glutamic acid, salicylic acid, muconic acid, and the like. In preferred embodiments, the acid is HCL.

In some embodiments, the method comprises purifying the compound of Formula (II). In some embodiments, the method comprises removing ammonium salts, such as tri ethyl ammonium salts, from the compound of Formula (II). In certain embodiments, the compound of Formula (II) is provided as a crystalline solid. In some embodiments, the method comprises crystallizing the compound of Formula (II) according to the methods described herein.

In some embodiments, the method comprises adding a solvent to the compound of Formula (II) to form a mixture, such as a solution. In some embodiments, the solvent is a polar solvent. Polar solvents include polar groups, which may be selected from, e.g., hydroxyl, carbonyl, ether, ester, amine, amide, and carboxyl groups. In some embodiments, the solvent comprises water. In preferred embodiments, the alcohol R—OH is the reaction solvent. In preferred embodiments, the solvent is a linear or branched alcohol, such as methanol, ethanol, propanol, or butanol, including branched and unbranched isomers thereof. In more preferred embodiments, the solvent is propanol, such as 1-propanol or 2-propanol. In some embodiments, the temperature of the mixture comprising the compound of Formula (II) is about −5 to about 10° C., about −5 to about 5° C., or about 0° C.

In some embodiments, the method comprises mixing the compound of Formula (II) and the alcohol. In certain embodiments, the mixing step occurs for about 12 to about 72 hours, about 12 to about 48 hours, or about 12 to about 24 hours. In some embodiments, the mixture comprising the compound of Formula (II) is about −5 to about 10° C., about −5 to about 5° C., or about 0° C. throughout the mixing step.

In some embodiments, the method comprises adding a base. In various embodiments, the base is added after about 12 to about 72 hours, about 12 to about 48 hours, or about 12 to about 24 hours. In some embodiments, the base is added until the pH of the reaction mixture is about 4 to about 5. In certain embodiments, the base is an amine base. In certain such embodiments, the base is a trialkylamine base. In preferred embodiments, the base is triethylamine. In further embodiments, the method comprises adding a seed crystal of the compound of Formula (I) to the reaction mixture.

In various embodiments, the method comprises purifying the resulting product (i.e., a compound of Formula (I)). In some embodiments, purifying the product comprises chromatography. In other embodiments, purifying the product does not comprise chromatography. In preferred embodiments, purifying the product comprises crystallizing the compound of Formula (I) according to the methods described herein. In preferred embodiments, the compound of Formula (I) is provided as a crystalline solid described herein.

Methods of Treatment, Diseases, Disorders, and Conditions

Provided herein are methods of modulating NAD levels in a subject in need thereof, comprising administering a compound, a crystalline solid, and/or a composition described herein. Any compound, crystalline solid, or composition described herein may be used in the manufacture of a medicament for the treatment of any diseases or conditions disclosed herein.

Provided herein are methods of treating a disease or disorder associated with NAD biosynthesis, comprising administering a compound, a crystalline solid, and/or a composition described herein.

Provided herein are methods for using the disclosed compounds, crystalline solids, and pharmaceutical compositions thereof. The disclosed compounds, crystalline solids, and pharmaceutical compositions thereof can be useful for a variety of therapeutic applications including, for example, treating and/or reducing a wide variety of diseases and disorders including, for example, diseases or disorders related to aging or stress, diabetes, obesity, neurodegenerative diseases, ataxia and related muscle disorders, acute organ failure, viral symptoms such as cytokine storm, cardiovascular disease, blood clotting disorders, inflammation, cancer, and/or flushing, etc. The methods comprise administering to a subject in need thereof a disclosed compound, crystalline solid, and/or pharmaceutical composition thereof. The disclosed compounds, crystalline solids, and pharmaceutical compositions thereof can be useful for increasing or maintaining NAD levels in certain tissues or cells while decreasing NAD levels in other tissues or cells. In various embodiments, the disclosed compounds, crystalline solids, and pharmaceutical compositions thereof can be used to selectively decrease NAD levels in some tissues or cells, while decreasing NAD levels to a lesser extent in other tissues or cells.

The disclosed compounds, crystalline solids, and pharmaceutical compositions thereof can also be used to treat a disease or disorder associated with inflammation. Exemplary inflammatory conditions include, for example, multiple sclerosis, rheumatoid arthritis, psoriatic arthritis, degenerative joint disease, spondyloarthropathies, gouty arthritis, systemic lupus erythematosus, juvenile arthritis, rheumatoid arthritis, osteoarthritis, osteoporosis, diabetes (e.g., insulin dependent diabetes mellitus or juvenile onset diabetes), menstrual cramps, cystic fibrosis, inflammatory bowel disease, irritable bowel syndrome, Crohn's disease, mucous colitis, ulcerative colitis, gastritis, esophagitis, pancreatitis, peritonitis, Alzheimer's disease, shock, ankylosing spondylitis, gastritis, conjunctivitis, pancreatitis (acute or chronic), multiple organ injury syndrome (e.g., secondary to septicemia or trauma), myocardial infarction, atherosclerosis, stroke, reperfusion injury (e.g., due to cardiopulmonary bypass or kidney dialysis), acute glomerulonephritis, vasculitis, thermal injury (i.e., sunburn), necrotizing enterocolitis, granulocyte transfusion associated syndrome, and/or Sjogren's syndrome. Exemplary inflammatory conditions of the skin include, for example, eczema, atopic dermatitis, contact dermatitis, urticaria, scleroderma, psoriasis, and dermatosis with acute inflammatory components.

In other embodiments, the disclosed compounds, crystalline solids, and/or a pharmaceutical composition thereof can be used to treat skin conditions. Exemplary skin conditions that may be treated in accordance with the methods described herein include disorders or diseases associated with or caused by inflammation, sun damage, or natural aging. For example, the compositions find utility in the treatment of contact dermatitis (including irritant contact dermatitis and allergic contact dermatitis), atopic dermatitis (also known as allergic eczema), actinic keratosis, keratinization disorders (including eczema), epidermolysis bullosa diseases, exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In other embodiments, the disclosed compounds, crystalline solids, and pharmaceutical compositions thereof may be used for the treatment of wounds and/or burns to promote healing, including, for example, first-, second- or third-degree burns and/or thermal, chemical or electrical burns.

The disclosed compounds, crystalline solids, and pharmaceutical compositions thereof can also be administered to a subject suffering from an acute disease, e.g., damage to an organ or tissue, e.g., a subject suffering from stroke or myocardial infarction or a subject suffering from a spinal cord injury, or a subject undergoing transplant of a solid organ such as the liver or kidney. In some embodiments, the compounds, crystalline solids and pharmaceutical compositions thereof may be administered to a subject suffering from acute kidney injury (AKI), also known as acute renal failure (ARF). Subjects suffering from or at risk of suffering from AKI may be screened for kidney function, for example by testing for abnormal levels of serum creatinine. Subjects may be treated prophylactically or in response to acute kidney injury, such as stage 1 AKI. Subjects undergoing solid organ transplant may be treated prophylactically, or post-transplant, or the individual organs may be treated outside the body prior to transplant, as a form of organ preservation. Subjects undergoing surgery other than organ transplant, such as biopsy or resection or repair of traumatic injury, may be treated prophylactically, or post-surgery.

The disclosed compounds, crystalline solids and pharmaceutical compositions thereof may also be used for a subject suffering from or likely to suffer from chronic damage or chronic disease in a solid organ, such as the kidney or liver. In some embodiments, crystalline solids and pharmaceutical compositions thereof may be administered to a subject suffering from chronic kidney disease, such as end stage renal failure, or such as nephropathy, or such as diabetic nephropathy. In some embodiments, crystalline solids and pharmaceutical compositions thereof may be administered to a subject suffering from chronic liver disease, such as chronic infection, cirrhosis, or liver cancer, in order to repair or limit further damage to the liver. In some embodiments, crystalline solids and pharmaceutical compositions thereof may be administered to repair an alcoholic's liver, or to stabilize or repair damage from non-alcoholic steatohepatitis (NASH) or non-alcoholic fatty liver disease (NAFLD).

In certain embodiments, a compound, crystalline solid, or pharmaceutical composition as disclosed herein may be used for treating or preventing a disease or condition induced or exacerbated by cellular senescence in a subject; methods for decreasing the rate of senescence of a subject, e.g., after onset of senescence; methods for extending the lifespan of a subject; methods for treating or preventing a disease or condition relating to lifespan; methods for treating or preventing a disease or condition relating to the proliferative capacity of cells; and methods for treating or preventing a disease or condition resulting from cell damage or death. In certain embodiments, the method does not act by decreasing the rate of occurrence of diseases that shorten the lifespan of a subject. In certain embodiments, a method does not act by reducing the lethality caused by a disease, such as cancer.

In certain embodiments, a compound, crystalline solid, or pharmaceutical composition as disclosed herein may be administered to a subject in order to generally increase the lifespan of its cells and to protect its cells against stress and/or against apoptosis. Treating a subject with a compound or crystalline solid described herein may be similar to subjecting the subject to hormesis, i.e., mild stress that is beneficial to organisms and may extend their lifespan.

In other embodiments, provided herein is a method for treating a cardiovascular disease by administering to a subject in need thereof a disclosed compound, crystalline solids, and/or a pharmaceutical composition thereof. Cardiovascular diseases that can be treated using the disclosed compounds, crystalline solids, and pharmaceutical compositions thereof include cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable using compositions and methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated include those related to platelet aggregation, the retinal arterioles, the glomerular arterioles, the vasa nervorum, cardiac arterioles, and associated capillary beds of the eye, the kidney, the heart, and the central and peripheral nervous systems. The disclosed compounds, crystalline solids, and pharmaceutical compositions thereof may also be used for increasing HDL levels in plasma of an individual.

The disclosed compounds, crystalline solids, and pharmaceutical compositions thereof may be administered to subjects who have recently received or are likely to receive a dose of radiation or toxin. In one embodiment, the dose of radiation or toxin is received as part of a work-related or medical procedure, e.g., working in a nuclear power plant, flying an airplane, an X-ray, CAT scan, or the administration of a radioactive dye for medical imaging; in such an embodiment, the compound or crystalline solid is administered as a prophylactic measure. In other embodiments, the radiation or toxin exposure is received unintentionally, e.g., as a result of an industrial accident, habitation in a location of natural radiation, terrorist act, or act of war involving radioactive or toxic material. In such a case, the disclosed compounds, crystalline solids, and pharmaceutical compositions thereof are preferably administered as soon as possible after the exposure to inhibit apoptosis and the subsequent development of acute radiation syndrome.

In other embodiments, the disclosed compounds, crystalline solids, and pharmaceutical compositions thereof may be useful for treating age-related disorders, such as, for example, cancer. Exemplary cancers that may be treated using the disclosed compounds, crystalline solids, and pharmaceutical compositions thereof include those of the brain and kidney; hormone-dependent cancers including breast, prostate, testicular, and ovarian cancers; lymphomas, and leukemias. Other diseases that can be treated include autoimmune diseases, e.g., systemic lupus erythematosus, scleroderma, and arthritis, in which autoimmune cells should be removed.

Viral infections such as herpes, HIV, adenovirus, and HTLV-1 associated malignant and benign disorders can also be treated by administration of the disclosed compounds, crystalline solids, and pharmaceutical compositions thereof.

In some embodiments, the disclosed compounds, crystalline solids, and pharmaceutical compositions thereof can be used to treat patients suffering from infectious diseases—such as COVID-19 and other viral infections—including those experiencing symptoms such as cytokine release syndrome (cytokine storm). In some embodiments, the compounds, crystalline solids, and pharmaceutical compositions thereof alleviate or prevent cytokine storm without necessarily treating the underlying viral infection (e.g., COVID-19). Cytokine release syndrome is an acute systemic inflammatory syndrome that can arise from a variety of causes. In particular, cytokine storms have been described in COVID-19 as well as other severe viral syndromes (SARS, MERS). A subset of patients exhibits notably elevated cytokines, and severe patients can also exhibit much higher levels of IL6, CRP, ferritin, D-dimer, and other markers, as well as lymphopenia (reduced count of CD4+ and CD8+ T cells). For example, in one report, a D-dimer level on admission of >2.0 ug/ml identified a subset of patients likely to die (12/67>=2.0 vs 1/267<2.0, sensitivity 92.3%, specificity 83.3%) ("D-dimer levels on admission to predict in-hospital mortality in patients with Covid-19." Zhang L, Yan X, Fan Q, et al. J Thromb Haemost. 2020 Apr. 19). NAD modulates the NLRP3 inflammasome release of IL-1ß, by which it may modulate the cytokine storm. NAD levels are known to decline with age, which may also contribute to worse outcomes for older COVID-19 patients. An aspect of the present disclosure provides a method of treating COVID-19 in a human patient comprising administering thee disclosed compounds, crystalline solids, and pharmaceutical compositions thereof to said patient in the absence of administration of zinc sulfate, betaine, or a mixture thereof.

In some embodiments, the disclosed compounds, crystalline solids, and pharmaceutical compositions thereof can be used to treat patients suffering from neurodegenerative diseases, and traumatic or mechanical injury to the central nervous system (CNS) or peripheral nervous system (PNS). Examples of neurodegenerative diseases include, but are not limited to, ataxia, Alzheimer's disease (AD), a dementia other than Alzheimer's Disease, Parkinson's disease (PD), Huntington disease (HD), amyotrophic lateral sclerosis (ALS; Lou Gehrig's disease), diffuse Lewy body disease, chorea-acanthocytosis, primary lateral sclerosis, multiple sclerosis (MS), ocular diseases (ocular neuritis), spinal muscle atrophy, chemotherapy-induced neuropathies (e.g., from vincristine, paclitaxel, bortezomib), diabetes-induced neuropathies, and Friedreich's ataxia.

In some embodiments, the disclosed compounds, crystalline solids, and pharmaceutical compositions thereof may be used for treatment of skeletomuscle disorders, muscular disorders, and conditions including muscle loss, atrophy, and sarcopenia.

In other embodiments, the disclosed compounds, crystalline solids, and pharmaceutical compositions thereof may be used for reducing appetite and/or increasing satiety, thereby causing weight loss or avoidance of weight gain. A subject in need of such a treatment may be a subject who is overweight, obese or a subject likely to become overweight or obese.

In other embodiments, the disclosed compounds, crystalline solids, and pharmaceutical compositions thereof may be used to treat a subject who has cachexia or may be likely to develop cachexia. A method may further comprise monitoring in the subject the state of the disease. Methods for promoting appetite and/or weight gain may include, for example, prior identifying a subject as being in need of decreased fat or lipid metabolism, e.g., by weighing the subject and determining the BMI of the subject. The method may also include monitoring the subject, e.g., during and/or after administration of the disclosed compounds, crystalline solids, or pharmaceutical compositions thereof. The administering can include one or more dosages, e.g., delivered in boluses or continuously. Monitoring can include evaluating a hormone or a metabolite. Exemplary hormones include leptin, adiponectin, resistin, and insulin. Exemplary metabolites include triglycerides, cholesterol, and fatty acids.

In some embodiments, the disclosed compounds, crystalline solids, and pharmaceutical compositions thereof may be used for treating a metabolic disorder, such as insulin-resistance, a pre-diabetic state, type II diabetes, and/or complications thereof. Administration of the disclosed compounds, crystalline solids, and pharmaceutical compositions thereof may increase insulin sensitivity and/or decrease insulin levels in a subject. A subject in need of such a treatment may be a subject who has insulin resistance or other precursor symptom of type II diabetes, who has type II diabetes, or who is likely to develop any of these conditions. For example, the subject may be a subject having insulin resistance, e.g., having high circulating levels of insulin and/or associated conditions, such as hyperlipidemia, dyslipogenesis, hypercholesterolemia, impaired glucose tolerance, high blood glucose sugar level, other manifestations of syndrome X, hypertension, atherosclerosis, and lipodystrophy.

Provided herein is a process for regulating the concentration of blood glucose in a mammal. As utilized herein, regulating the concentration of blood glucose refers to any increase, decrease, and/or maintenance in or of the concentration of blood glucose as compared to a previously determined level.

The methods of treatment disclosed herein are also directed to methods of regulating the circadian clock, thereby regulating or affecting biological functions that are regulated by (sometimes also said to be affected by, affiliated with, or mediated by) the activity of the circadian clock. Typically, these biological functions display a pattern of activity and inactivity that is generally repeated approximately every 24 hours, oscillating between "active" and "inactive" states during the 24 hour period.

Thus, the present disclosure provides methods of regulating the activity of the circadian clock by administering to a mammal in need thereof a compound, crystalline solid, or pharmaceutical composition as disclosed herein. Generally, the regulation of the activity of the circadian clock is the result of the regulation of CLOCK:BMAL1, which is achieved according to the present methods by regulating the activity of SIRT1. The activity of SIRT1 is generally regulated according to the present methods by administration of a compound, crystalline solid, or pharmaceutical composition as disclosed herein, and in certain embodiments, by administration of a compound or crystalline solid that affects the NAD pathway. The regulation of the circadian clock thereby permits regulation of activities mediated by the circadian clock.

According to the present disclosure, the activity of the circadian clock may be increased, decreased, or maintained by the administration of a compound, crystalline solid, or pharmaceutical composition as disclosed herein. Accordingly, biological functions (sometimes also referred to as biological activities) that are regulated by the activity of the circadian clock may also be increased, decreased, or maintained. In addition, these biological functions may also be time shifted; that is to say, an activity that typically occurs during a particular period, such as for example, during daytime or daylight hours (sometimes also referred to as the light cycle) or during the night or nighttime hours (sometimes also referred to as the dark cycle) may be shifted such that the activity occurs during the dark or light cycle, respectively, instead.

In various embodiments, disclosed herein are methods of differentially modulating nicotinamide adenine dinucleotide (NAD) levels in two or more tissues or cell types. Such methods may comprise administering a compound, crystalline solid, or composition as disclosed herein, wherein said administering induces a differential response in NAD levels in a first tissue or cell type compared to a second tissue or cell type. In various embodiments, a differential response in NAD levels is selected from at least a 10% difference in NAD levels, at least a 20% difference in NAD levels, at least a 30% difference in NAD levels, at least a 40% difference in NAD levels, at least a 50% difference in NAD levels, at least a 60% difference in NAD levels, at least a 70% difference in NAD levels, at least a 80% difference in NAD levels, at least a 90% difference in NAD levels, at least a 100% difference in NAD levels, at least a 200% difference in NAD levels, at least a 300% difference in NAD levels, at least a 400% difference in NAD levels, at least a 500% difference in NAD levels, at least a 600% difference in NAD levels, at least a 700% difference in NAD levels, at least a 800% difference in NAD levels, at least a 900% difference in NAD levels, and at least a 1000% difference in NAD levels. In various embodiments, a differential response in NAD levels is an increase in NAD levels of at least 10%, 20%, 30%, 40%, 50%, 60%, 70%, 80%, 90%, 100%, 200%, 300%, 400%, 500%, 600%, 700%, 800%, 900%, or 1000% in a first tissue or cell type compared to untreated NAD levels or NAD levels before treatment, and a simultaneous decrease in NAD levels of at least 10%, 20%, 30%, 40%, 50%, 60%, 70%, 80%, 90%, 100%, 200%, 300%, 400%, 500%, 600%, 700%, 800%, 900%, or 1000% in a second tissue or cell type compared to untreated NAD levels or NAD levels before treatment. In various embodiments, a differential response in NAD levels is a maintenance in NAD levels within 10% in said first tissue or cell type compared to untreated NAD levels, and a simultaneous decrease in NAD levels of at least 10%, 20%, 30%, 40%, 50%, 60%, 70%, 80%, 90%, 100%, 200%, 300%, 400%, 500%, 600%, 700%, 800%, 900%, or 1000% in a second tissue or cell type compared to untreated NAD levels. In various embodiments, a differential response in NAD levels is a reduction in NAD levels of at least 10% in a first tissue or cell type compared to untreated NAD levels, and a simultaneous decrease in NAD levels in a second tissue or cell type compared to untreated NAD levels, wherein the decrease in the second tissue or cell type is at least 10%, 20%, 30%, 40%, 50%, 60%, 70%, 80%, 90%, 100%, 200%, 300%, 400%, 500%, 600%, 700%, 800%, 900%, or 1000% more reduction than the reduction in the first tissue or cell type. In various embodiments, the first tissue or cell type is normal tissue or cells, and the second tissue or cell type is neoplastic or cancerous.

Methods of treatment of cancer disclosed herein include treatment of an individual in need thereof. Exemplary cancers that may be treated using the disclosed compounds, crystalline solids, and pharmaceutical compositions thereof include those of the brain and kidney; hormone-dependent cancers including breast, prostate, testicular, and ovarian cancers; lymphomas, and leukemias. In various embodiments, the cancer may be a common type of cancer in males, such as lung cancer, prostate cancer, colorectal cancer and stomach cancer. In various embodiments, the cancer may be a common type of cancer in females, such as breast cancer, colorectal cancer, lung cancer and cervical cancer. In various embodiments, the cancer may be a skin cancer, such as melanoma, squamous cell carcinoma, or basal cell carcinoma. In various embodiments, the cancer may be a common type of cancer in children, such as acute lymphoblastic leukemia, brain tumors, or non-Hodgkin lymphoma. In various embodiments, the method exhibits a selective cytostatic or cytotoxic effect, wherein the effect is demonstrated by decreased viability of neoplastic or cancerous tissue or cells compared to untreated neoplastic or cancerous tissue or cells.

Methods include the situation where a first tissue or cell type is normal tissue or cells, and the method is a treatment for the promotion of the health or increase in biological activity of the first tissue or cell type in an individual in need thereof. In various embodiments, the treatment does not induce an increase in the risk of a cancer diagnosis in a treated individual. Preferably, the treatment reduces the risk of a cancer diagnosis in an individual receiving treatment.

Various methods include treating or suppressing cancer in an individual in need thereof, where the method comprises administering a compound, crystalline solid, or composition as described herein. In various embodiments, disclosed herein are methods of increasing or maintaining healthy tissue or cells in an individual in need thereof without increasing the risk of growth of neoplastic or cancerous tissue or cells, such methods comprising administering a compound, crystalline solid, or composition as described herein.

In various embodiments, described herein are methods of increasing or maintaining healthy tissue or cells in an individual in need thereof while suppressing the growth of neoplastic or cancerous tissue or cells, such methods comprising administering a compound, crystalline solid, or composition as described herein. In various embodiments, the disclosed methods include methods of increasing or maintaining nicotinamide adenine dinucleotide (NAD) levels in at least one healthy tissue or cell type, such methods comprising administering a compound, crystalline solid, or composition described herein to the healthy tissue or cell type. In various embodiments, described herein are methods of reducing the viability of at least one cancerous tissue or cell type, such method comprising administering a compound, crystalline solid, or composition as described herein to the cancerous tissue or cell type.

In addition, methods as described herein include methods of modulating the level of NAD in at least one tissue or cell type in a mixture of tissues or cell types, such methods comprising targeted delivery of a compound, crystalline solid, or composition as described herein to the desired tissue or cell type. In various embodiments, the targeted delivery is non-systemic.

Compositions and Pharmaceutical Compositions

Also provided herein are compositions of the disclosed compounds and crystalline solids. In certain embodiments, the composition comprises 1) a crystalline solid comprising a compound of Formula (I) or Formula (II) or a salt thereof, and 2) one or more pharmaceutically acceptable excipients. In other embodiments, the composition comprises 1) a compound of Formula (I) or Formula (II) or a salt thereof, and 2) one or more pharmaceutically acceptable excipients.

In some embodiments, the composition is a solution. For example, in some embodiments a crystalline solid comprising a compound of Formula (I) or Formula (II) is dissolved in a solvent or carrier to form a solution of the compound of Formula (I) or Formula (II). In preferred embodiments, the crystalline solid is of a purity such that the resulting solution is pure or substantially pure and/or free or substantially free of one or more impurities.

In certain preferred embodiments, the present disclosure provides a composition comprising a compound of Formula (I) or Formula (II) or crystalline solid comprising a compound of Formula (I) or Formula (II), wherein the composition is pure or substantially pure. In certain preferred embodiments, the composition is greater than about 90% pure. More preferably, the composition is greater than about 95% pure, or even more preferably greater than about 98% pure, e.g. greater than about 98% pure. In some embodiments, the percentage is by weight.

In preferred embodiments, the composition comprises less than about 5% impurities, less than about 2% impurities, less than about 1% impurities, or less than about 0.5% impurities. For example, in preferred embodiments where the composition comprises a compound of Formula (I), the composition comprises less than about 5% propyl nicotinate, less than about 2% propyl nicotinate, less than about 1% propyl nicotinate, less than about 0.5% propyl nicotinate, less than about 0.1% propyl nicotinate, or less than about 0.01% propyl nicotinate. In preferred embodiments where the composition comprises a compound of Formula (II), the composition comprises less than about 5% nicotinic acid riboside, less than about 2% nicotinic acid riboside, less than about 1% nicotinic acid riboside, less than about 0.5% nicotinic acid riboside, less than about 0.1% nicotinic acid riboside, or less than about 0.01% nicotinic acid riboside. In some embodiments, the percentage is by weight.

In some embodiments, the pharmaceutically acceptable excipient is selected from an anti-adherent, binder, coating, dye, disintegrant, flavoring agent, glidant, lubricant, preservative, sorbent, sweetener, syrups, elixirs, dispersant, diluent, filler, granulating agent, coating agent, wax, suspending agent, wetting agent, thickener and vehicle and combinations thereof. In some embodiments, the excipient is a solid excipient.

In some embodiments, the pharmaceutically acceptable excipient is present in an amount of at least about 5% by weight, at least about 10% by weight, at least about 15% by weight, at least about 20% by weight, at least about 25% by weight, at least about 30% by weight, at least about 35% by weight, at least about 40% by weight, at least about 45% by weight, at least about 50% by weight, at least about 55% by weight, or at least about 60% by weight of the composition. In some embodiments, the pharmaceutically acceptable excipient is present in an amount of at least about 20% by weight, at least about 25% by weight, at least about 30% by weight, at least about 35% by weight, or at least about 40% by weight, preferably at least about 30% by weight of the composition. In other embodiments, the pharmaceutically acceptable excipient is present in an amount of at least about 50% by weight of the composition. The pH of the formulations can range from about 3 to about 11, but is ordinarily about 7 to about 10.

In some embodiments, the composition is in a solid form selected from a tablet, a pill, a capsule, a caplet, a troche, granules, powders, sachet, dry powder inhalation form, a chewable, a pastille, and a lozenge. In certain embodiments, the composition is in the form of a tablet. In other embodiments, the composition is in a form of a hard or soft gelatin capsule.

The compounds and crystalline solids of this disclosure are formulated with conventional carriers and excipients, which can be selected in accord with ordinary practice. Tablets can contain excipients, glidants, fillers, binders and the like. All formulations will optionally contain excipients such as those set forth in the *Handbook of Pharmaceutical Excipients* (1986). Suitable excipients are also listed in the US Food and Drug Administration Inactive Ingredients Database. Excipients include ascorbic acid and other antioxidants, chelating agents such as EDTA, carbohydrates such as dextran, hydroxyalkylcellulose, hydroxyalkylmethylcellulose, stearic acid and the like.

While it is possible for active pharmaceutical ingredients to be administered alone, it may be preferable to present them as pharmaceutical formulations. The formulations, both for veterinary and for human use, of the disclosure comprise at least one active ingredient, as above defined, together with one or more acceptable carriers therefor and optionally other therapeutic ingredients. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound or crystalline solid may also be formulated for inhalation. In certain embodiments, a compound crystalline solid may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

Formulations of the present disclosure suitable for oral administration may be presented as discrete units such as capsules, cachets or tablets, each containing a predetermined amount of the active ingredient as a powder or granules. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Pharmaceutical formulations according to the present disclosure comprise a compound or crystalline solid according to the disclosure together with one or more pharmaceutically acceptable carriers or excipients and optionally other therapeutic agents. Pharmaceutical formulations containing the active ingredient may be in any form suitable for the intended method of administration. When intended for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques, including microencapsulation, to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the disclosure contain the active material(s) in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia; and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin. Liquid formulations may also include eye drops or other forms of delivery to the surface of the eye or adjacent locations such as tear ducts. Liquid formulations may include intravenous formulations, excipients, and carriers such as saline solution, or buffered solution, and the packaging or containers for such formulations, for injection or infusion or the like.

Dispersible powders and granules of the disclosure suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The amount of active ingredient that may be combined with the carrier material to produce a single dosage form will vary depending upon the subject treated and the particular mode of administration. For example, a time-release formulation intended for oral administration to humans may contain approximately 1 to approximately 1000 mg of active material compounded with an appropriate and convenient amount of carrier material which may vary from about 5% to about 95% of the total compositions (weight:weight). The pharmaceutical composition can be prepared to provide easily measurable amounts for administration.

Although the dosage will vary depending on the symptoms, age and body weight of the patient, the nature and severity of the disorder to be treated or prevented, the route of administration and the form of the drug, in general, a daily dosage of from 0.01 to 3000 mg of the compound or crystalline solid is recommended for an adult human patient, and this may be administered in a single dose or in divided doses. In general, the compositions of this disclosure may be provided in an aqueous solution containing about 0.1-30% w/v of a compound or crystalline solid disclosed herein, among other substances, for parenteral administration. Typical dose ranges are from about 0.01 to about 50 mg/kg of body weight per day, given in 1 single or 2-4 divided doses. In certain embodiments, the compounds and/or crystalline solids described herein are administered in an amount from about 1 to about 3000 mg per day, from about 100 to about 1000 mg per day, or from about 250 to about 750 mg per day. If desired, the effective daily dose of the active compound or crystalline solid may be administered as one, two, three, four, five, six or more sub-doses administered separately at appropriate intervals throughout the day, optionally, in unit dosage forms. In some embodiments, the compounds and/or crystalline solids described herein are administered one, two, three, four, five, six or more times per day. The amount of active ingredient which can be combined with a carrier material to produce a single dosage form will generally be that amount of the compound and/or crystalline solid which produces a therapeutic effect.

Formulations suitable for intrapulmonary or nasal administration have a particle size for example in the range of about 0.1 to about 500 microns, such as about 0.5, about 1, about 30, or about 35 microns etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above, the formulations of this disclosure may include other agents conventional in the art having regard to the type of formulation in question, for example those suitable for oral administration may include flavoring agents.

In some embodiments, the amount of the compound and/or crystalline solid in the composition is about 0.001% by weight up to 100% by weight.

In some embodiments, the compound and/or crystalline solid is the sole active pharmaceutical ingredient in the composition. Alternatively, the compound and/or crystalline solid is formulated in a composition with one or more additional active pharmaceutical ingredients. When formulated as the sole active pharmaceutical ingredient, the compound and/or crystalline solid may be administered individually, or as part of a regimen with one or more separately formulated active pharmaceutical ingredients.

When conjointly administered either in the same formulation or as part of a regimen with one or more separately formulated active pharmaceutical ingredients, the additional active pharmaceutical ingredient may be selected from compounds in the NAD pathway, such as nicotinic acid (NA), nicotinamide (Nam), nicotinamide mononucleotide (NMN), nicotinamide riboside (NR), nicotinic acid riboside (NAR), nicotinamide adenine dinucleotide (NAD/NADH), nicotinamide adenine dinucleotide phosphate (NADP), and nicotinic acid adenine dinucleotide (NaAD). In some embodiments, compounds of Formula I and II are conjointly administered. In some embodiments, the additional active pharmaceutical ingredient is an amorphous solid. In some embodiments, the additional active pharmaceutical ingredient is a crystalline solid. In some embodiments, the additional active pharmaceutical ingredient is amorphous NMN. In some embodiments, the additional active pharmaceutical ingredient is crystalline NMN.

The invention now being generally described, it will be more readily understood by reference to the following examples, which are included merely for purposes of illustration of certain aspects and embodiments of the present invention, and are not intended to limit the invention.

EXAMPLES

Example 1.1: Preparation of Compound 2

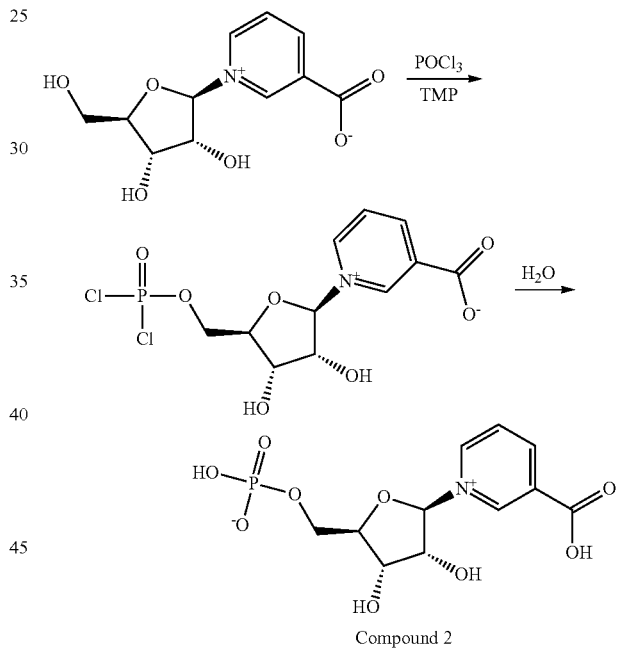

Compound 2

Figure 4:
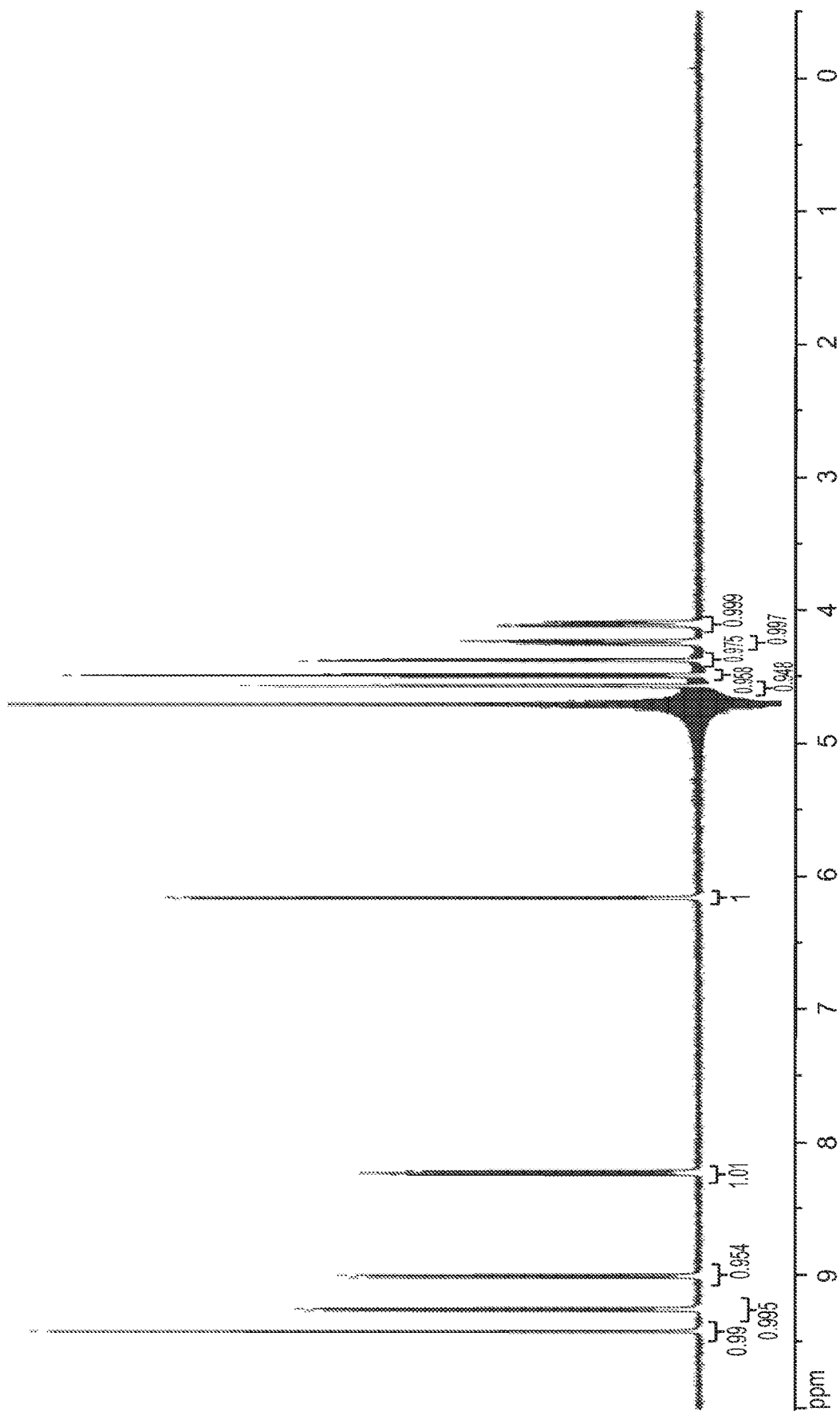
FIG. 4 shows an experimentally obtained proton NMR spectrum of Compound 2 in D$_2$O. The x-axis shows the chemical shift (ppm).

A 50 mL recovery flask was charged with 1.00 g (3.92 mmoL) of nicotinic acid riboside and purged with argon. To this was added 6 mL of trimethylphosphate, then stirring was initiated and the reaction was cooled with an ice bath. Next, 0.73 mL (7.84 mmol) of phosphorus oxychloride was added. After 30 minutes, the reaction was complete as determined by LC/MS. The reaction was added dropwise to 10 mL of ice-cold water. After addition was complete, the mixture was concentrated in vacuo to remove about 9 g of solvent. The concentrated mixture was then added dropwise to a stirred, ice-cold solution of 3.2 mL (23.0 mmol) of triethylamine in 50 mL of 1-propanol, giving a mixture with pH=3, as determined by pH paper. The suspension was stirred for 1 h, then the solid precipitate was filtered and rinsed with 1-propanol, giving a first crop of crude Compound 2. After the filtration was complete, solids formed in the supernatant. The filtrate was stirred for 72 h, then the suspension was filtered, and the precipitate was rinsed with 1-propanol to give a second crop of crude Compound 2. The second crop was dried in vacuo, the weight was 1.00 g while still damp. $^1$H and $^{31}$P NMR analysis showed that the second crop was of better purity than the first crop. The second crop was used as seed material for subsequent experiments. See FIG. 4.

$^1$H-NMR (500 MHz; D$_2$O): δ 9.42 (s, 1H), 9.25 (d, J=6.3 Hz, 1H), 9.00 (d, J=8.0 Hz, 1H), 8.22 (dd, J=7.8, 6.5 Hz, 1H), 6.16 (d, J=5.3 Hz, 1H), 4.58-4.56 (m, 1H), 4.49 (t, J=5.1 Hz, 1H), 4.37 (dd, J=5.0, 2.8 Hz, 1H), 4.26-4.22 (m, 1H), 4.12-4.08 (d, d, d 1H, J=12.0, 5.1, 2.2 Hz)

Example 1.2A: Crystallization of Compound 2

To 100 mg of amorphous Compound 2 (prepared separately) was added 300 microliters of water. To this was added 350 microliters of 1-propanol, giving a cloudy solution. The second crop of Compound 2 from the experiment above was used to seed the mixture. After several hours, crystals formed in the vial. The mixture was not filtered and remained as a slurry.

Example 1.2B: Crystallization of Compound 2

A 2.00 g quantity of amorphous Compound 2 (prepared separately) was dissolved in 6 mL of water, then 7 mL of 1-propanol was added to give a cloudy solution. An additional 2 mL of water was added to give a clear solution. The second crop of Compound 2 from the experiment above as used to seed the mixture, but no crystals formed. An additional 0.2 mL of n-propanol was added to give a cloudy mixture. This was allowed to stir for one day, giving no crystals. The mixture was then seeded with a drop of the slurry from the second experiment to prepare Compound 2 crystals, giving rapid crystallization. This was allowed to stir for two days at ambient temperature. The solids were filtered and washed with 15 mL of (2:1 v:v) 1-propanol:water, 15 mL of 1-propanol, then 2×15 mL of methyl tert-butyl ether. The sample was dried under high vacuum at ambient temperature for 1 hour to give 1.92 g (96% mass recovery) of a white solid. The water solubility of the isolated product was about 20 mg/mL (50:1 w:w water:Compound 2), in contrast to the starting Compound 2 which was freely soluble in water (3:1 water:Compound 2).

Example 1.2C: Crystallization of Compound 2

Figure 2C:
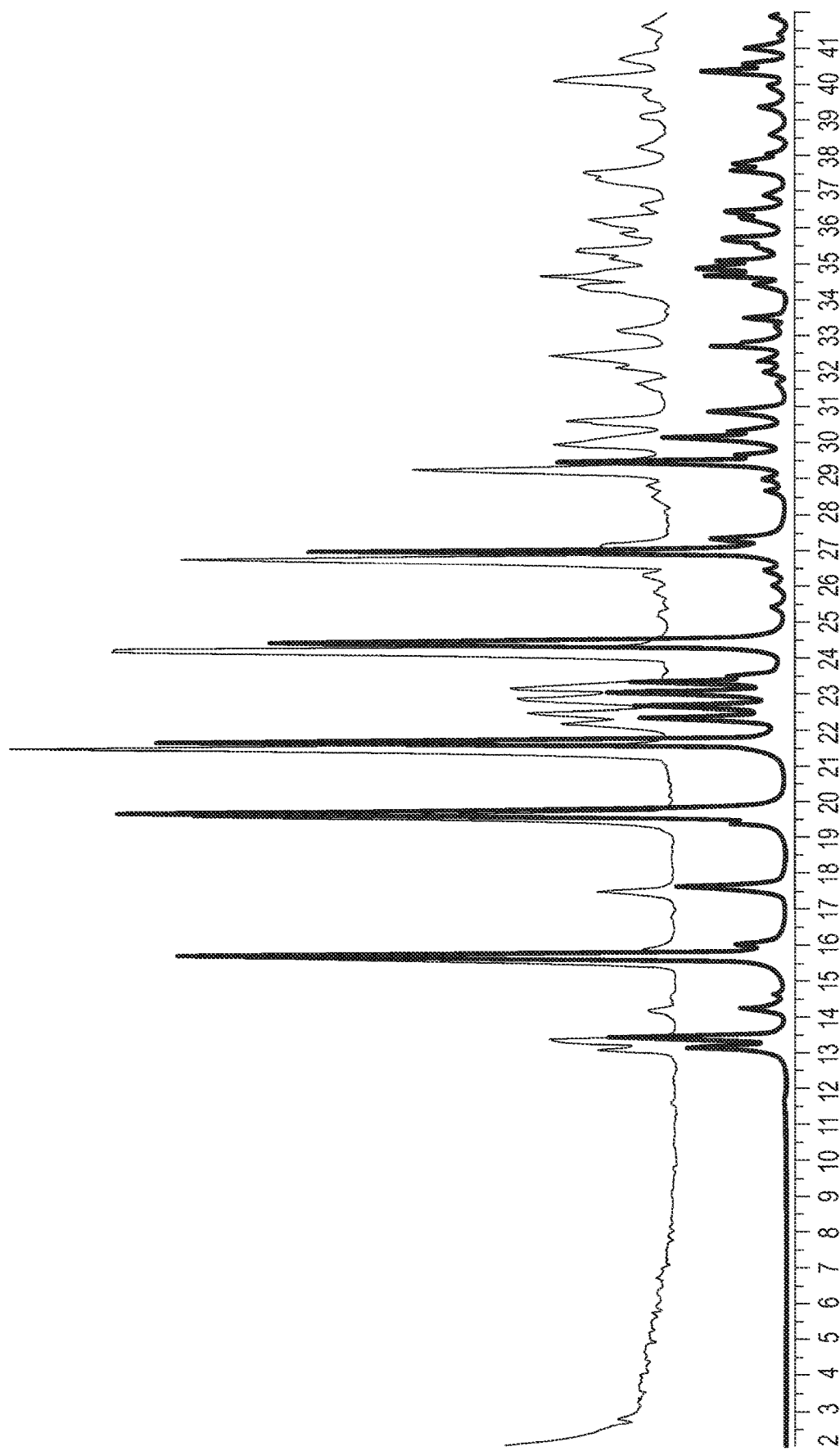
FIG. 2C shows an overlay where the top pattern is the experimental diffractogram for Compound 2; and the bottom pattern is the calculated diffractogram from a single crystal x-ray structure. Slight differences in the simulated and experimental diffractograms are attributable to lattice variations with temperature and preferred orientation.

A 500 mg quantity of amorphous Compound 2 was dissolved in 1.5 mL of water. The sample dissolved completely, then crystals began to form. Crystals were allowed to grow without agitation. The water was decanted, then the solids were dried under high vacuum. Single crystal x-ray diffraction quality crystals of Compound 2 were prepared. These crystals were used to generate the XRPD signature for Compound 2 crystals (FIG. 2), and also to obtain the single crystal x-ray structure of Compound 2 (FIG. 2C).

Example 2.1: Preparation of Compound 1

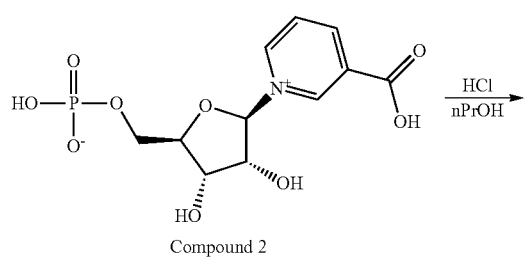

Compound 2

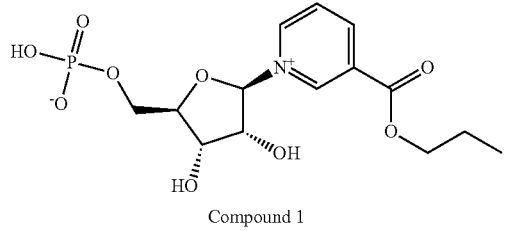

Compound 1

Figure 3:
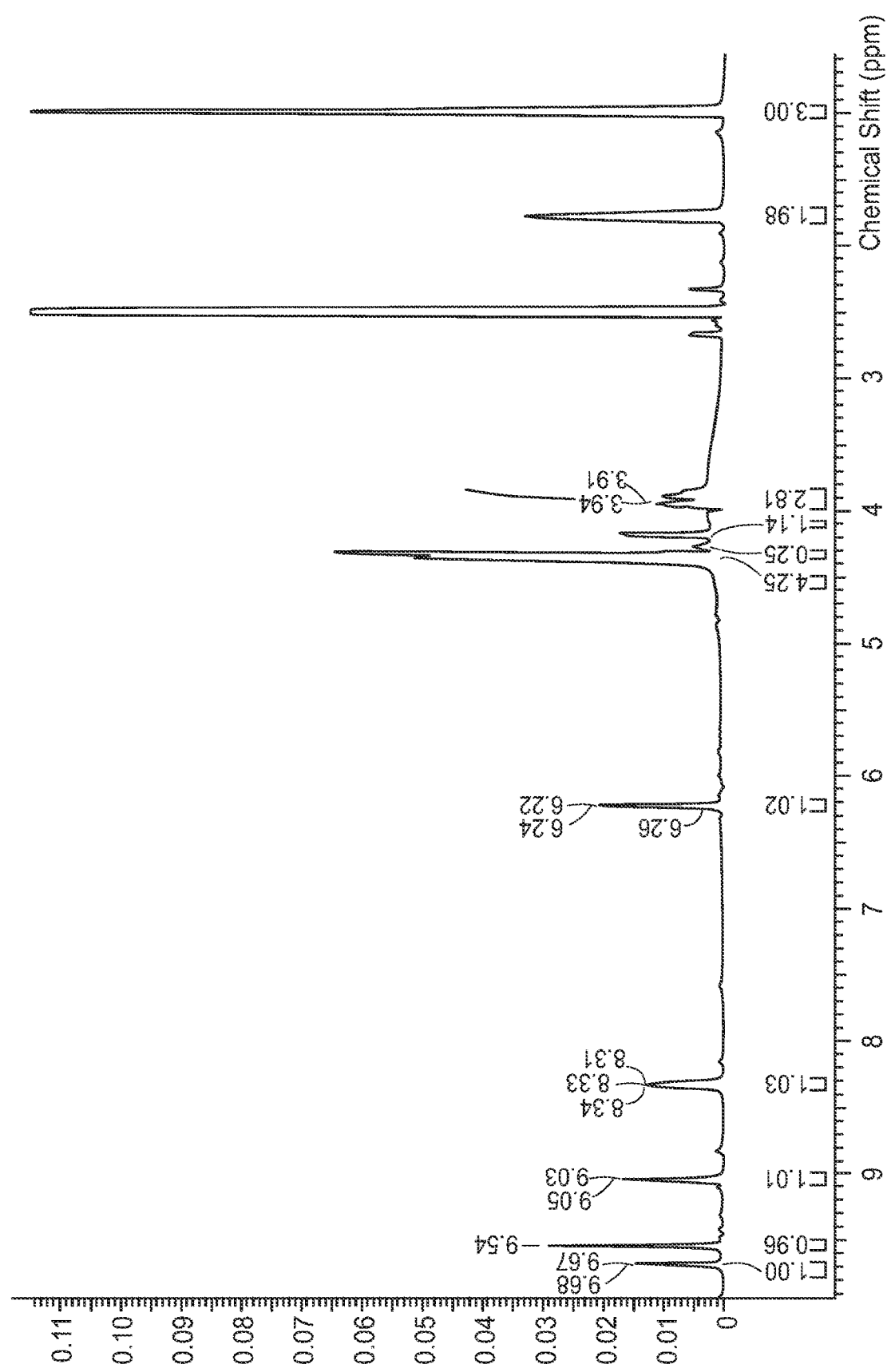
FIG. 3 shows an experimentally obtained proton NMR spectrum of Compound 1 in DMSO-d6. The x-axis shows the chemical shift (ppm).

Compound 2 was filtered from 1-propanol prior to use, and charged to a 500 mL recovery flask and purged with argon. The solids were suspended in 1-propanol and cooled in an ice bath. HCl gas was bubbled in the reaction mixture. The solids dissolved as the gas was bubbled into the suspension. The reaction was removed from the ice bath and stirred at room temperature over three days. When no starting material remained by LC/MS, the reaction mixture was concentrated down on a rotary evaporator until an oil was obtained. An aliquot was placed under high vacuum for 30 minutes. The aliquot did not foam up. A sample of this was taken for LC/MS. The oil was diluted with 10 mL of 1-propanol and cooled with an ice bath. A total of 1.5 mL of triethylamine was added to bring the pH to 4-5. The addition of triethylamine caused a significant amount of precipitate to form. 40 mL of 1-propanol was added to dissolve all of the precipitate. Compound 1 seed crystals were added to the solution. Over time, the solution became cloudy and a precipitate was observed forming. The suspension was allowed to stir at room temperature overnight. After 4 hours on the high vac, a sample of the aliquot was taken for LC/MS. The contents of the flask appear more crystalline and filterable compared to a "milky" suspension. Solids were filtered. The filter cake was washed twice with 10 mL of 1-propanol each followed by two 10 mL washes of MTBE. A sample of the 1-propanol filtrate was taken for LC/MS. The solids were transferred to a vial. The damp weight was ~1.2 g. Placed under high vacuum for 1 hour. Obtained 1.23 g (55% yield) of a white solid. A sample was taken for LC/MS, $^1$H and $^{31}$P NMR. See FIG. 3.

Example 2.2A: Polymorph Screening

Amorphous Compound 1 was screened for polymorphs according to the conditions provided in Table 1, with treatment between Observation 1 and Observation 2 including maturation cycling between 0° C. (1 hr) and −20° C. (7 hrs) for 4 days, with the results as shown.

TABLE 1

| Solvent | Volume added at −20° C./ volumes | Observation 1 | Observation 2 | Treatment | XRPD |
|---|---|---|---|---|---|
| n-Heptane | 30 | x | White paste round sides of vial | Filter | Amorphous |
| Ethyl acetate | 30 | x | White paste round sides of vial | Filter | Amorphous |
| Isopropyl acetate | 30 | x | White paste round sides of vial | Filter | Amorphous |
| MIBK | 30 | x | White paste round sides of vial + suspension | Filter | Amorphous |
| 2-Propanol | 30 | x | White paste round sides of vial + suspension | Filter | Amorphous |
| MEK | 30 | x | Pale yellow solid | Filter | Amorphous |
| Acetone | 30 | x | White paste round sides of vial + suspension | Filter | Amorphous |
| Ethanol | 5 | x | White paste – gum- redissolved at 5° C. | — | — |
| tert-Butylmethyl ether | 30 | x | White paste round sides of vial + suspension | Filter | Amorphous |
| 2-Methyl-1-propanol | 30 | x | Thin white suspension + some pale yellow solid | Filter | Amorphous |
| 1-propanol | 30 | x | Pale yellow gum | Filter | — |
| Hexane | 30 | x | White paste round sides of vial | Filter | Amorphous |
| Methanol | 5 | x | Solution | Freezer | — |
| Toluene | 30 | x | Gummy looking material | Filter | Amorphous |
| Tetrahydrofuran | 30 | x | White suspension | Filter | Amorphous |
| Dichloromethane | 30 | x | Solution | Freezer | — |
| Acetonitrile | 30 | x | Gummy looking material-gum | Filter | — |
| 1-methoxy-2-propanol | 30 | x | Solution | Freezer | — |
| 1,2-Dimethoxyethane | 30 | x | White suspension with white paste around the sides | Filter | Amorphous |
| 2-Methoxyethanol | 5 | x | Solution | Freezer | — |
| Nitromethane | 30 | x | Bright yellow gum | Filter | — |
| 10% Water/ EtOH | 15 | x | Solution | Freezer | — |
| 10% Water/ IPA | 5 | x | Gummy solution | Filter | — | x = suspension

Example 2.2B: Salt Screening

Amorphous Compound 1 was screened for polymorphs according to Table 2. Compound 1 (15 mg) was weighed into an HPLC vial and magnetic stir bar was added. The compound was dissolved in ca. 15 vol (200 μl) EtOH at 5° C. while stirring at 500 rpm. Once dissolved, a molar equivalent of counterion was added and stirred at 5° C. (45 μl of 1M stock or 90 μl of 0.5M stock). The samples were cooled to −20° C. at 1° C./min but remained solutions. The solutions were allowed to slowly evaporate through a needle in the vial cap while at 5° C.

TABLE 2

| Counterion | Upon addition at 5 C. | Upon cooling to −20 C. | Slow evaporation at 5 C. | XRPD |
|---|---|---|---|---|
| Sodium chloride | P | P | Clear gum | Amorphous + NaCl peaks |
| Potassium hydroxide | P | P | Glassy solid | No trace |
| Sodium hydroxide | P | P | Glassy solid | No trace |
| L-arginine | P | P | Glassy solid | Amorphous |
| Choline hydroxide | P | P | Sticky dark gum | N/P |
| L-lysine monohydrate | P | P | Glassy solid | Amorphous |

TABLE 2-continued

| Counterion | Upon addition at 5 C. | Upon cooling to −20 C. | Slow evaporation at 5 C. | XRPD |
|---|---|---|---|---|
| Ammonium hydroxide | P | P | Glassy solid | Amorphous |
| N-methylglucamine | P | P | Glassy solid | Amorphous |

Key: P = solution,
N/P = not performed

Example 2.2C: Co-Crystal Screening

Amorphous Compound 1 was screened for polymorphs according to Table 3. The Compound 1 (25 mg) was weighed into an HPLC vial and two grinding balls added. To this was added 1 mol equivalent of coformer (as a solid). The mixture was initially ground at 500 rpm, 2 hours on a Fritsch planetary mill and then solids recovered were analysed by XRPD. No crystallized material was obtained, and the resulting solids were wetted with a drop of THF (7.5 µl) and ground for 2 hours at 500 rpm on the Fritsch planetary mill. Observations were made post-grinding and XRPD performed on solids recovered.

TABLE 3

| Coformer | Coformer (mg) | After dry grinding 2 hrs | XRPD after dry grinding | After grinding with THF drop | XRPD after grinding with THF |
|---|---|---|---|---|---|
| Propyl gallate | 14.1 | Yellow/green gum | Amorphous + coformer | Yellow/green sticky gum | N/P |
| Methylparaben | 10.1 | Gum | Amorphous + coformer | Sticky gum | N/P |
| Urea | 4 | Sticky gum | N/P | Sticky gum | N/P |
| Succinic acid | 7.8 | Sticky gum | N/P | Sticky gum | N/P |
| Tartaric acid | 9.95 | Gum | Amorphous + coformer | Sticky gum | N/P |
| Stearic acid | 18.85 | Solid | Amorphous + coformer | Solid | Amorphous + coformer |
| L-Malic acid | 8.9 | Sticky gum | N/P | Sticky gum | N/P |
| Benzoic acid | 8.1 | Solid | Amorphous + coformer | Sticky gum | N/P |
| Fumaric acid | 7.7 | Solid | Amorphous + coformer | Solid | Amorphous + coformer |
| Caffeic acid | 11.9 | Solid | Amorphous + coformer | Solid | Amorphous + coformer |
| Caffeine | 12.9 | Solid | Amorphous + coformer | Solid | Amorphous + coformer |
| Theobromine | 11.9 | Solid | Amorphous + coformer | Solid | Amorphous + coformer |

Key: P = solution,
N/P = not performed

Example 2.2D: Crystal Form of Compound 1

Compound 1 (150 mg) was dissolved in 10 vol (1.5 ml) of absolute EtOH at room temperature with stirring. After 3 minutes a precipitate started to form. The sample was stirred for a further 15 minutes before being filtered and dried using positive pressure. The sample was then placed in vacuum oven under vacuum at room temperature for 30 minutes. The sample was then left in the fume hood overnight in a vial capped with perforated aluminum foil before being characterized. XPD pattern was obtained according to FIG. 1A. See also FIG. 1B. Percentage yield=ca. 6300 and purity of 98.700 by HPLC. Upon storage for seven days at 40° C./750% RH, the material was a sticky solid, with purity of 96.4% by HPLC. The sample is a fine white powder that is stable at room temperature, a small quantity of solvent is entrapped, but analysis indicates sample is an anhydrous, non-solvated solid. Sample is stable at humidity conditions up to 700% RH.

FIG. 1C is a representation of a crystal lattice unit cell for Compound 1 with the following attributes:
Crystal system: Orthorhombic
Space group: $P2_12_12_1$
Unit cell dimensions: a=12.53610(10) Å α=90°
b=12.59210(10) Å β=90°
c=20.9476(2) Å γ=90°
Volume=3306.70(5) Å$^3$
$R_{factor}$=2.80%
Z=8 Z'=2
Temperature of collection=100 K The data for Compound 1 were obtained by single crystal X-ray diffraction, and the structure was solved by direct methods and refined using a least-squares refinement. Atom assignment and location in the crystal structure were assigned based on the electron density observed in the Fourier difference map converging to a model with a good fit to the experimental data. Non-hydrogen atoms were refined anisotropically giving anisotropic displacement parameters (thermal ellipsoids) which can be seen in the ORTEP image (FIG. 1C).

Example 2.2E: Scale-Up of Crystal Form of Compound 1

Amorphous Compound 1 (1.23 g) was weighed into a 20 ml vial and treated with 7 vol (8.60 ml) of methanol to give a clear solution. This solution was stirred at 400 rpm at 35° C. on a 'polar bear' apparatus. The solution was supersaturated by addition of 0.5 vol (615 μl) of TBME and then seeded using previously crystallized material (ca. 60 mg) which were sustained in the solution. The sample was then cooled to 25° C. at 0.1° C./min prior to anti-solvent addition. Addition of 2.6 vol (3.2 ml) of TBME was performed using a syringe pump over 50 minutes (1 μl/sec). The suspension was then cooled to 5° C. at 0.1° C./min. Samples were held at 5° C. for an hour prior to isolation using a Buchner funnel under vacuum. The sample was dried under vacuum for 20 mins and then further dried overnight in the vacuum oven. XPD pattern was obtained according to FIG. 1A. See also FIG. 1B. Percentage yield=ca. 45% and purity of 97.9% by HPLC.

Example 3: Stability Study of Compound 2

Amorphous and crystalline forms of Compound 2 were prepared and stored under stressed conditions to compare the stability of the respective forms, as indicated in Table 4. At T=0, amorphous Compound 2 was assayed at 97.3% AUC and the crystalline Compound 2 was assayed at 99%. Samples were sealed in jars containing saturated salt solutions to produce the required relative humidity, namely, ammonium nitrate for RH=600%; sodium chloride for RH=75%; and saturated potassium nitrate for RH=970. Solid phosphorus pentoxide was used for RH=0%. HPLC data were collected using an Agilent 1290 System equipped with a Waters Atlantis T3 Cis Column (3 um, 100×4.6 mm) with an in-line guard column. Mobile Phase A: 200 mM ammonium carbonate (pH 3.8); Mobile Phase B: 95:5 MeOH: Mobile Phase A. Pumping is at 1 mL/min. The gradient is 0% B for 5 minutes, followed by a 20-minute gradient to 100% B, and finally a hold for 3 minutes. Relevant data are collected via DAD at 254 nm.

The results in Table 4 show that the crystalline form of Compound 2 has improved stability compared to an amorphous form of Compound 2.

INCORPORATION BY REFERENCE AND EQUIVALENTS

All publications and patents mentioned herein are hereby incorporated by reference in their entirety as if each individual publication or patent was specifically and individually indicated to be incorporated by reference. In case of conflict, the present application, including any definitions herein, will control.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A crystalline solid comprising Compound 1:

having 2θ values 16.1, 20.1, and 24.5.

2. The crystalline solid of claim 1, wherein the solid is anhydrous.

3. The crystalline solid of claim 1, wherein said crystalline solid contains residual non-solvated solvent or residual non-hydrated water.

| Sample | Conditions | AUC 1 day | AUC 7 days | AUC 14 days | Comments |
|---|---|---|---|---|---|
| Amorphous | RT, 0% RH | 97.3 | 96.6 | 96.8 | |
| Crystalline | | 96.7 | 99 | 99.2 | |
| Amorphous | RT, 60% RH | 97.1 | 96.6 | 97.4 | collapsed after 1 day |
| Crystalline | | 99 | 98.9 | 98.9 | |
| Amorphous | RT, 75% RH | 96.5 | 97.1 | 98.1 | collapsed after 1 day |
| Crystalline | | 99 | 98.9 | 98.8 | |
| Amorphous | RT, 97% RH | 97 | 97.1 | 97.7 | |
| Crystalline | | 98.9 | 98.9 | 99 | |
| Amorphous | 50 C., 0% RH | N/A | 91.5 | 89.9 | |
| Crystalline | | 99 | 98.6 | 98.6 | |
| Amorphous | 50 C., 60% RH | 85.9 | 85 | 67.2 | Discolored after 1 day, black after 7 days |
| Crystalline | | 99 | 98.9 | 98.7 | |
| Amorphous | 50 C., 75% RH | 97 | 89.8 (OS) | 91.1 | Discolored after 1 day. Very dark brown after 1 week |
| Crystalline | | 99 | 98.6 | 98.3 | Discolored after 1 day. Tan solid after 1 week |
| Amorphous | 50 C., 97% RH | 97.3 | 74.1 | 26.2 | Melted to a semi-solid after 1 day. Completely melted after 1 week |
| Crystalline | | 98.7 | 97.1 | 93 | Discolored but still powdery. |

Legend: AUC = % Area under the curve @ 254 nm;
RH = Relative Humidity;
OS = Off-scale 4. The crystalline solid of claim 1, wherein said crystalline solid is non-hygroscopic.

5. A composition comprising the crystalline solid of claim 1, wherein the composition comprises less than about 5% by weight propyl nicotinate.

6. A composition comprising the crystalline solid of claim 1, wherein the composition comprises less than about 5% by weight Compound 2:

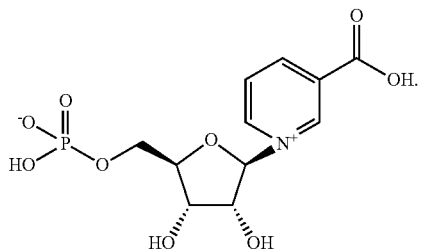

7. A composition comprising the crystalline solid of claim 1, said composition comprising at least about 90% by weight of Compound 1.

8. A pharmaceutical composition comprising the crystalline solid of claim 1, and further comprising one or more pharmaceutically acceptable excipients.

9. A method for preparing the crystalline solid of claim 1, comprising:
   a) dissolving Compound 1 in a solvent to form a solution; and
   b) crystallizing Compound 1 from the solution to form the crystalline solid;
   wherein the solvent is methanol or ethanol.

10. The method of claim 9, wherein the solvent is methanol.

11. The method of claim 9, wherein the solution is anhydrous.

12. The method of claim 9, wherein the solvent is heated to a temperature during the dissolving step from about 30° C. to about 40° C.

13. The method of claim 9, wherein crystallizing comprises forming a supersaturated solution from the solution, wherein the supersaturated solution is supersaturated with respect to Compound 1.

14. The method of claim 13, wherein forming the supersaturated solution comprises adding an anti-solvent to the solution, lowering the temperature of the solution, reducing the volume of the solution, or any combination thereof.

15. The method of claim 9, wherein crystallizing comprises adding a seed crystal to the solution, wherein the seed crystal comprises Compound 1.

16. A method of purifying Compound 1:

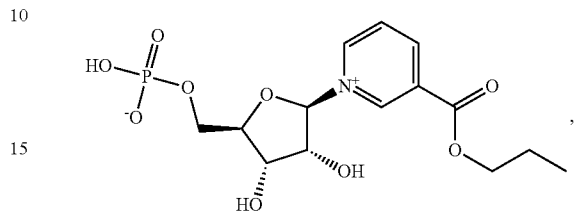

said method comprising:
   a) dissolving Compound 1 in a solvent to form a solution; and
   b) crystallizing the compound from the solution to form a solid of greater purity than the purity of Compound 1 dissolved in step (a), wherein said solid of greater purity is the crystalline solid of claim 1;
   wherein the solvent is methanol or ethanol.

17. The method of claim 16, where step (a) is performed with amorphous Compound 1, and wherein said solid of greater purity in step (b) has purity of greater than about 95% by weight.

18. A method of increasing NAD levels in a subject, the method comprising administering a crystalline solid according to claim 1 to the subject.

19. A method of treating or reducing the occurrence of a disease or disorder in a subject in need thereof, the method comprising administering a crystalline solid according to claim 1 to the subject.

20. A method of increasing NAD levels in a subject, the method comprising administering a composition according to claim 8 to the subject.

21. A method of treating or reducing the occurrence of a disease or disorder in a subject in need thereof, the method comprising administering a composition according to claim 8 to the subject.

* * * * *